US010403489B2

United States Patent
Reed et al.

(10) Patent No.: US 10,403,489 B2
(45) Date of Patent: Sep. 3, 2019

(54) SYSTEMS AND APPROACHES FOR SEMICONDUCTOR METROLOGY AND SURFACE ANALYSIS USING SECONDARY ION MASS SPECTROMETRY

(71) Applicant: NOVA MEASURING INSTRUMENTS INC., Santa Clara, CA (US)

(72) Inventors: David A. Reed, Belmont, CA (US); Bruno W. Schueler, San Jose, CA (US); Bruce H. Newcome, Sunnyvale, CA (US); Rodney Smedt, Los Gatos, CA (US); Chris Bevis, Los Gatos, CA (US)

(73) Assignee: NOVA MEASURING INSTRUMENTS INC., Santa Clara, CA (US)

( * ) Notice: Subject to any disclaimer, the term of this patent is extended or adjusted under 35 U.S.C. 154(b) by 0 days.

(21) Appl. No.: 16/039,292

(22) Filed: Jul. 18, 2018

(65) Prior Publication Data

US 2018/0330935 A1 Nov. 15, 2018

Related U.S. Application Data

(63) Continuation of application No. 15/550,014, filed as application No. PCT/US2016/017370 on Feb. 10, 2016, now Pat. No. 10,056,242.

(Continued)

(51) Int. Cl.
*H01J 49/14* (2006.01)
*H01L 21/66* (2006.01)
(Continued)

(52) U.S. Cl.
CPC ............ *H01J 49/142* (2013.01); *G01N 23/22* (2013.01); *G01Q 10/04* (2013.01); *H01J 49/26* (2013.01); *H01L 22/12* (2013.01)

(58) Field of Classification Search
USPC ........................................ 250/305, 306, 307
See application file for complete search history.

(56) References Cited

U.S. PATENT DOCUMENTS 3,894,233 A 7/1975 Tamura
4,633,084 A 12/1986 Gruen et al.
(Continued)

FOREIGN PATENT DOCUMENTS

CN 107438891 A 12/2017
EP 0278736 A2 8/1988
(Continued)

OTHER PUBLICATIONS

PCT International Search Report of the International Searching Authority for International Application No. PCT/US2016/017370, 4 pages (dated Jul. 29, 2016).

(Continued)

*Primary Examiner* — Kiet T Nguyen
(74) *Attorney, Agent, or Firm* — Womble Bond Dickinson (US) LLP; Joseph Bach, Esq.

(57) ABSTRACT

Systems and approaches for semiconductor metrology and surface analysis using Secondary Ion Mass Spectrometry (SIMS) are disclosed. In an example, a secondary ion mass, spectrometry (SIMS) system includes a sample stage. A primary ion beam is directed to the sample stage. An extraction lens is directed at the sample stage. The extraction lens is configured to provide a low extraction field for secondary ions emitted from a sample on the sample stage. A magnetic sector spectrograph is coupled to the extraction lens along an optical path of the SIMS system. The magnetic (Continued)

sector spectrograph includes an electrostatic analyzer (ESA) coupled to a magnetic sector analyzer (MSA).

22 Claims, 20 Drawing Sheets

Related U.S. Application Data

(60) Provisional application No. 62/114,521, filed on Feb. 10, 2015, provisional application No. 62/114,519, filed on Feb. 10, 2015, provisional application No. 62/114,524, filed on Feb. 10, 2015.

(51) Int. Cl.
*G01N 23/22* (2018.01)
*G01Q 10/04* (2010.01)
*H01J 49/26* (2006.01)

(56) References Cited

U.S. PATENT DOCUMENTS

| | | | |
|---|---|---|---|
| 5,034,605 A | 7/1991 | Bayly | |
| 5,164,594 A | 11/1992 | Thompson et al. | |
| 6,078,045 A * | 6/2000 | Maul | G01N 23/2258 250/281 |
| 8,304,725 B2 | 11/2012 | Komuro et al. | |
| 10,056,242 B2 | 8/2018 | Reed et al. | |
| 2002/0134949 A1 * | 9/2002 | Gerlach | H01J 37/08 250/492.21 |
| 2005/0091863 A1 | 5/2005 | Chuang et al. | |
| 2005/0139772 A1 | 6/2005 | Hasegawa et al. | |
| 2006/0192106 A1 | 8/2006 | Haydent et al. | |
| 2007/0040118 A1 | 2/2007 | Cheng et al. | |
| 2007/0221845 A1 | 9/2007 | Komuro et al. | |
| 2008/0265159 A1 | 10/2008 | Hatakeyama et al. | |
| 2009/0140763 A1 | 6/2009 | Kim | |
| 2011/0248156 A1 | 10/2011 | Komatsu et al. | |

FOREIGN PATENT DOCUMENTS

| | | |
|---|---|---|
| FR | 2784750 A1 | 4/2000 |
| JP | S62-160650 A | 7/1987 |
| JP | 2010-211973 A | 9/2010 |
| JP | 2018-512718 A | 5/2018 |
| WO | WO 2008/050251 A1 | 5/2008 |
| WO | 2014/108376 A1 | 7/2014 |
| WO | 2016/130603 A1 | 8/2016 |
| WO | 2016/130690 A1 | 8/2016 |

OTHER PUBLICATIONS

PCT Written Opinion of the International Searching Authority for International Application No. PCT/US2016/017370, 9 pages (dated Jul. 29, 2016).

PCT International Preliminary Report on Patentability for PCT Application No. PCT/US2016/017370, 10 pgs. (dated Aug. 15, 2017).

Maheshwari, P., "Surface Characterization of Impurities in Superconducting Niobium for Radio Frequency (RF) Cavities used in Particle Accelerators," *Materials Science and Engineering,* Raleigh, NC; Aug. 14, 2012, pp. 1-236.

* cited by examiner

SYSTEMS AND APPROACHES FOR SEMICONDUCTOR METROLOGY AND SURFACE ANALYSIS USING SECONDARY ION MASS SPECTROMETRY

CROSS-REFERENCE TO RELATED APPLICATIONS

This patent application is a continuaton application of U.S. patent application Ser. No. 15/550,014, filed Aug. 9, 2017, entitled "SYSTEMS AND APPROACHES FOR SEMICONDUCTOR METROLOGY AND SURFACE ANALYSIS USING SECONDARY ION MASS SPECTROMETRY," which is a U.S. National Phase application under 35 U.S.C. § 371 of International Application No. PCT/US2016/017370, filed on Feb. 10, 2016, entitled SYSTEMS AND APPROACHES FOR SEMICONDUCTOR METROLOGY AND SURFACE ANALYSIS USING SECONDARY ION MASS SPECTROMETRY, which claims the benefit of U.S. Provisional Application No. 62/114,521, filed on Feb. 10, 2015; U.S. Provisional Application No. 62/114,519, filed on Feb. 10, 2015; and U.S. Provisional Application No. 62/114,524, filed on Feb. 10, 2015, the entire contents of which were incorporated by reference.

BACKGROUND

1) Field

Embodiments of the invention are in the field of semiconductor metrology and, in particular, systems and approaches for semiconductor metrology and surface analysis using Secondary Ion Mass Spectrometry (SIMS).

2) Description of Related Art

Secondary ion mass spectrometry (SIMS) is a technique used to analyze the composition of solid surfaces and thin films by sputtering the surface of the specimen with a focused primary ion beam and collecting and analyzing ejected secondary ions. The mass/charge ratios of these secondary ions are measured with a mass spectrometer to determine the elemental, isotopic, or molecular composition of the surface to a depth of 1 to 2 nanometers. Due to the large variation in ionization probabilities among different materials, SIMS is generally considered to be a qualitative technique, although quantitation is possible with the use of standards. SIMS is the most sensitive surface analysis technique, with elemental detection limits ranging from parts per million to parts per billion.

Generally, SIMS requires a high vacuum with pressures below $10^{-4}$ Pa. High vacuum is needed to ensure that secondary ions do not collide with background gases on their way to the detector (i.e., the mean free path of gas molecules within the detector must be large compared to the size of the instrument), and it also prevents surface contamination that otherwise may occur by adsorption of background gas particles during measurement.

Three basic types of ion guns are employed in SIMS analysis. In one, ions of gaseous elements are usually generated with duoplasmatrons or by electron ionization, for instance noble gases ($^{-10}$Ar, Xe$^-$), oxygen ($^{16}$O$^-$, $^{16}$O$^{2-}$, $^{16}$O$^{2-}$), or even ionized molecules such as SF$_5^-$ (generated from SF$_6$) or C$_{60}^-$ (fullerene). This type of ion gun is easy to operate and generates roughly focused but high current ion beams. A second source type, the surface ionization source, generates $^{133}$Cs$^-$ primary ions. Cesium atoms vaporize through a porous tungsten plug and are ionized during evaporation. Depending on the gun design, fine focus or high current can be obtained. A third source type, the liquid metal ion gun (LMIG), operates with metals or metallic alloys, which are liquid at room temperature or slightly above. The liquid metal covers a tungsten tip and emits ions under influence of an intense electric field. While a gallium source is able to operate with elemental gallium, recently developed sources for gold, indium and bismuth use alloys which lower their melting points. The LMIG provides a tightly focused ion beam (less than 50 nanometers) with moderate intensity and is additionally able to generate short pulsed ion beams. It is therefore commonly used in static SLMS devices.

The choice of the ion species and ion gun respectively depends on the required current (pulsed or continuous), the required beam dimensions of the primary ion beam and on the sample which is to be analyzed. Oxygen primary ions are often used to investigate electropositive elements due to an increase of the generation probability of positive secondary ions, while cesium primary ions often are used when electronegative elements are being investigated. For short pulsed ion beams in static SIMS, LMIGs are most often deployed for analysis. LMIGs can be combined with either an oxygen gun or a cesium gun during elemental depth profiling, or with a C$_{60}^-$ or gas cluster ion source during molecular depth profiling.

Depending on the SIMS type, there are three basic analyzers available: sector, quadrupole, and time-of-flight. A sector field mass spectrometer uses a combination of an electrostatic analyzer and a magnetic analyzer to separate the secondary ions by their mass to charge ratio. A quadrupole mass analyzer separates the masses by resonant electric fields, which allow only the selected masses to pass through. The time of flight mass analyzer separates the ions in a field-free drift path according to their velocity. Since all ions possess the same kinetic energy, the velocity and therefore time of flight varies according to mass. The time of flight mass analyzer requires pulsed secondary ion generation using either a pulsed primary ion gun or a pulsed secondary ion extraction. The time of flight mass analyzer is the only analyzer type able to detect all generated secondary ions simultaneously, and is the standard analyzer for static SIMS instruments.

In the field of surface analysis, it is usual to distinguish static SIMS and dynamic SIMS. Static SIMS is the process involved in surface atomic monolayer analysis, or surface molecular analysis, usually with a pulsed ion beam and a time of flight mass spectrometer. Meanwhile, dynamic SIMS is the process involved in bulk analysis, closely related to the sputtering process. Dynamic SIMS employs a DC primary ion beans and a magnetic sector or quadrupole mass spectrometer.

SIMS is a very powerful technique. However, advances are needed in the area of SIMS measurement equipment, systems, and methodologies.

SUMMARY

Embodiments of the present inversion includes systems and approaches for semiconductor metrology and surface analysis using Secondary Ion Mass Spectrometry (SIMS), In an embodiment, a secondary ion mass spectrometry (SIMS) system includes a sample stage. A primary ion beam is directed to the sample stage. An extraction lens is directed at the sample stage. The extraction lens is configured to provide a low extraction field for secondary ions emitted from a sample on the sample stage. A magnetic sector spectrograph is coupled to the extraction lens along an optical path of the SIMS system. The magnetic sector spectrograph includes an electrostatic analyzer (ESA) coupled to a magnetic sector analyzer (MSA)

In an embodiment, a method of measurement and control of the surface potential of a sample involves measuring kinetic energy of charged particles emitted from a surface of a sample. The method also involves determining a shift in kinetic energy of the charged particles. The surface potential of the surface of the sample is changed in response the shift in kinetic energy of the charged particles.

In an embodiment, a method of determining wafer backside contact resistance involves measuring a gap distance value of a surface of a wafer based on a comparison of a main capacitive sensor electrode driven with a first drive signal and a compensating capacitive sensor electrode driven with a second drive signal that is amplitude or phase shifted as compared to the first drive signal. A value of the second drive signal is measured. The value of the second drive signal is calibrated to a reference impendence standard to determine an impedance value of the wafer to ground. A contact resistance value is determined for the surface of the wafer based on the gap distance value and the impedance value of the wafer to ground.

DESCRIPTION OF THE EMBODIMENTS

Figure 1:
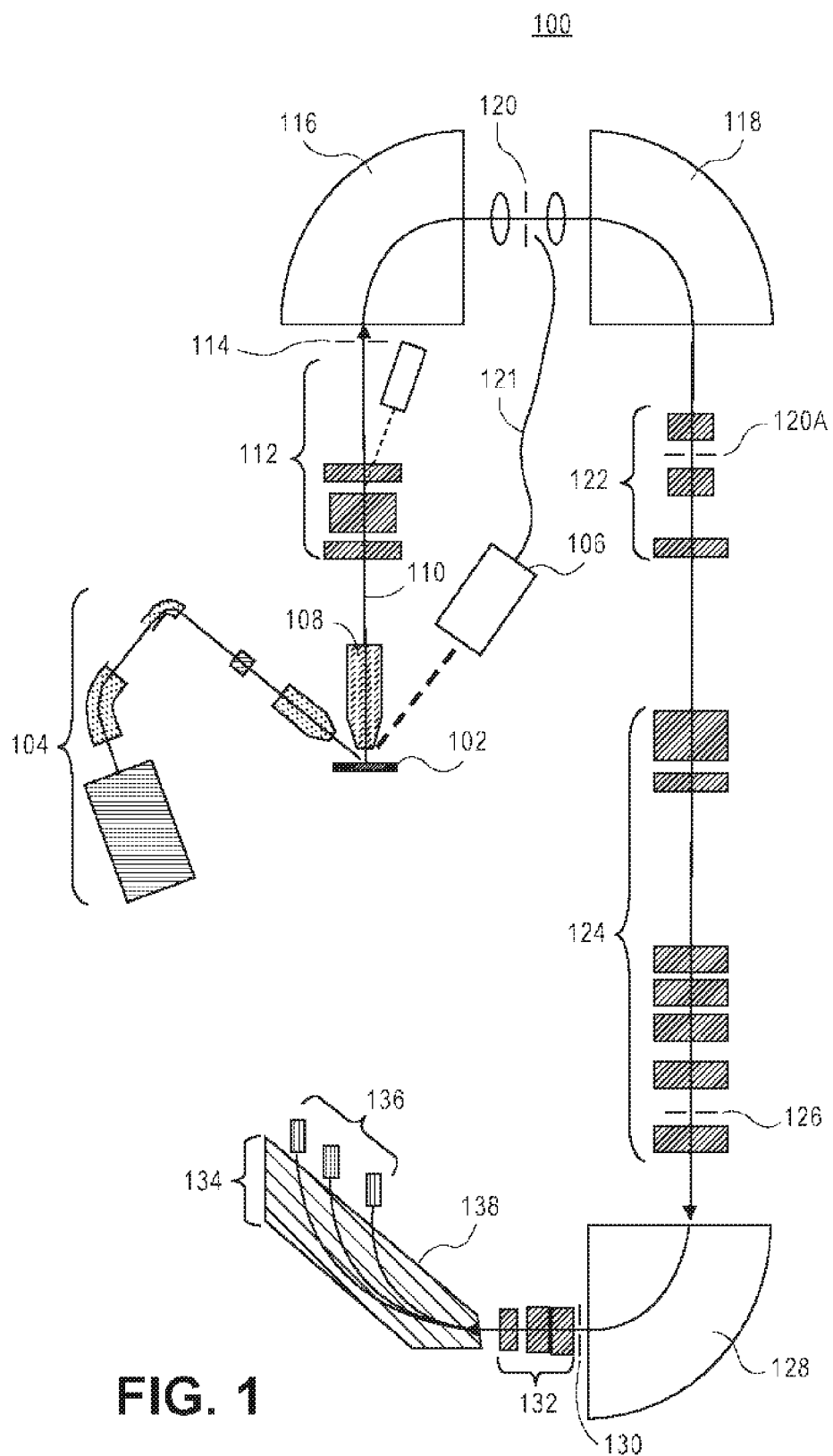
FIG. 1 illustrates a schematic layout of a SIMS measurement system, in accordance with an embodiment of the present invention.

Systems and approaches for semiconductor metrology and surface analysis using Secondary Ion Mass Spectrometry (SIMS) are described. In the following description, numerous specific details are set forth, such as SIMS analysis techniques and system configurations, in order to provide a thorough understanding of embodiments of the present invention. It will be apparent to one skilled in the art that embodiments of the present invention may be practiced without these specific details. In other instances, well-known features such as entire semiconductor device stacks are not described in detail in order to not unnecessarily obscure embodiments of the present invention. Furthermore, it is to be understood that the various embodiments shown in the Figures are illustrative representations and are not necessarily drawn to scale.

In a first aspect, embodiments of the present invention are directed to systems and methods for characterization and process control of structures on semiconductor wafers during manufacturing using Secondary Ion Mass Spectrometry (SIMS).

To provide context, state of the art semiconductor manufacturing entails many hundreds of process operations. Each process operations is subject to processing variations which can lead to variation and degradation of the performance of the finished device. As such, many measurements and inspections are performed during the manufacturing process to both ensure that a manufacturing operation has been executed correctly and within specification and also to provide feedforward and feedback to control the manufacturing process. Process control requires several key attributes that enable its effectiveness.

First, the cost of a measurement or inspection must be consistent with the economical manufacturing of devices. Practically, this means that the cost of a tool, the cost of consumables, the cost of ownership (including maintenance, calibration and other costs), its useful lifetime, the time required to take a measurement and the labor costs associated with its effective use are consistent with the manufacturing environment. Perhaps most importantly, it is critical that the characterization be nondestructive, as the cost of a semiconductor wafer during processing can be very high, and techniques which require destructive testing are not necessarily viable.

Second, the inspection and measurement must measure a sample which is directly relevant to the process control requirements. While techniques that can only measure "monitor" wafers, i.e., those wafers that have only undergone one or a few process operations, can be useful for tool qualification or coarse quality control, effective process control requires that the measured structures are as similar to actual device structures as possible and that measurement sampling can be as frequent as possible compared to the rate of process variation and drift.

Third, and perhaps most importantly, the inspection or measurement operation must have the desired information content, i.e., the required relevancy, resolution, accuracy and precision, required for process control.

To provide further context, Secondary Ion Mass Spectrometry (SIMS) is a well-known materials characterization technique which is capable of determining the depth profile of elemental composition with great accuracy and precision. Because of this unique capability, SIMS is widely used in materials science and analytical laboratory settings. While SIMS is currently used in an "offline" mode in semiconductor manufacturing, its use in "inline" process control is currently not viable due to its inability to address the practical issues outlined above. What is needed, therefore, is a Secondary Ion Mass Spectrometry system which provides the well known capabilities of SIMS while addressing the gaps which prevent its use in inline process control In order to satisfy the requirements of an in-line semiconductor manufacturing environment, several gaps in current SIMS designs must be addressed. Such gaps include particular challenges associated with measurement on typical product wafers, the time it takes to make the measurements, the availability/uptime of the tool (e.g., including time for calibration and verification), and the costs associated with the maintenance of the tool. Design specifics addressing one or more of the above issues are described below, in accordance with one or more embodiments of the present invention.

With respect to measurement on product wafers, performing a SIMS measurement on a product wafer entails three challenges that constrain the design. First, measurements on product wafers must typically be confined to a small designated area, such as a 50 μm by 50 μm pad. Second, at the same time, the manufacturer is typically interested in changes of composition over very small changes in depth. Third, there will be an unpredictable grounding path to the measurement site. In cases where the grounding is poor or non-existent the wafer will charge during the SIMS measurement, which leads to several problems including a deflection of the primary beam away from the intended site, a decrease in detected secondary ion signal, and a reduction in the ability to correctly identify and resolve secondary ion masses.

Addressing one or more of the above issues concerning measurements performed on product wafer, in accordance with an embodiment of the present invention, a SIMS approach described herein involves use of a low extraction Voltage at a secondary extraction lens of a SIMS measurement system. In particular, only a very weak electric field is used between the collection lens and the sample under measurement. Such an approach is contrary to a typical SIMS design which uses a strong electric field between the extraction lens and the sample to attract the secondary ions towards the lens and boost the number of collected ions. In one embodiment, the extraction field threshold is at most approximately 10 Volts/mm (as an absolute value).

FIG. 1 illustrates a schematic layout of a SIMS measurement system 100, in accordance with an embodiment of the present invention.

Referring to FIG. 1, the SIMS measurement system 100 includes an XY stage for holding a sample for analysis. Note that the stage need not be XY but could be any type such as XYZ, XY-Theta, R-Theta, etc. The XY stage may include a Faraday cup and fiducials, as described in greater detail below. A primary ion beam 104, which is generated by an ion source, refined by mass filters, and focused with a series of ion optics, is directed to the XY stage 102, e.g., at an incident angle of 40 degrees. A charge compensation electron gun 106 may also be directed at the XY stage, as is depicted in FIG. 1. An extraction lens 108 is positioned over the XY stage 102. In one embodiment, the extraction lens 108 has a portion near ground potential to maintain a small extraction field between the lens and the sample, typically of the order 10V/mm or less. A secondary ion beam 110 is collected from a sample on the XY stage into the extraction lens 108 and into collection/detection paths of SIMS system 100. It is to be appreciated that, although not depicted, the SIMS measurement system 100 of FIG. 1 may be included in an enclosure or chamber with vacuum environment.

Referring again to FIG. 1, an array of elements 112 may be included along the path 110 following the extraction lens 108. The array of elements 112 may include secondary-ion optics, deflectors and/or additional compensation mechanisms, as shown. The secondary ion beam 110 is then directed through a slit 114 and then into a first electrostatic analyzer (ESA) 116 and a second FSA 118. A slit 120 is placed between the first 116 and second 118 ESAs. The slit may be placed at the location where the beam 110 is spread by energy. In the SIMS system 100, the two ESAs 116 and 118 direct the beam toward the floor of the SIMS system 100. The two ESAs 116 and 118 also create a point at which the beam is spread according to energy, which can serve as a signal (e.g., along signal line 121) for the charge compensation system 106.

Referring again to FIG. 1, the beam 110 is then directed through a slit 120A and other features. For example wired slits and apertures 122 may be placed at several points along the beam path 110 to both limit/shape the beam and to monitor currents and beam positions. Many of these are on actuators to enable movement. Various other elements 124 such as optics and deflectors are included along the path 110 to keep the beam aligned and properly shaped.

Referring again to FIG. 1, the beam 110 is then directed through a slit 126 and into a third ESA 128, exit through slit 130 and through additional optics 132. The beam 110 is then directed into a magnetic sector analyzer (MSA) 134. The MSA 134 includes multiple (e.g., 10) detectors 136 along a focal plane 138, enabling detection of up to 10 species in parallel, as is described in greater detail below. It is to be appreciated that the MSA 134 and the third ESA 128 together constitute a magnetic sector spectrograph.

In one embodiment, referring again to system 100, by using a low extraction Voltage between the extraction lens 108 and the sample 102, as much as 80% a of a signal otherwise obtainable by a typical SIMS measurement is sacrificed. However, in return, it is much easier to accurately place the primary beam. For example, in systems where the extraction field is strong, the primary beam is deflected as much as tens or even hundreds of microns as it passes through the field, which means that the aim of the primary beam must be altered to compensate. This leads to a tricky control problem with typical SIMS measurements, making the precise rastering of the beam in a small 50 μm area very difficult.

Such deflection of the primary beam by the extraction field is more severe the lower the energy of the primary ions. Accordingly, under typical or conventional SIMS operation, there is incentive to maintain a high primary energy in order to minimize the beam deflection. However, high-energy primary beams lead to two effects that degrade the depth resolution. First, a high-energy primary beam penetrates more deeply into the sample leading to ions being created over a range of depths rather than at the surface. Second, the higher energies can drive surface atoms of the sample deep into the substrate, essentially smearing the material over depth. In an embodiment, in contrast to high-energy primary beams used in typical SIMS measurements, fine depth resolution required by the semiconductor industry is benefited from use of a low-energy primary beam. Accordingly, in one embodiment, the above described advantage of using a low-extraction field design is even greater when also designing for maximum depth resolution since otherwise severe deflection of a low-energy primary beam is mitigated by the low-extraction field design.

Figure 2:
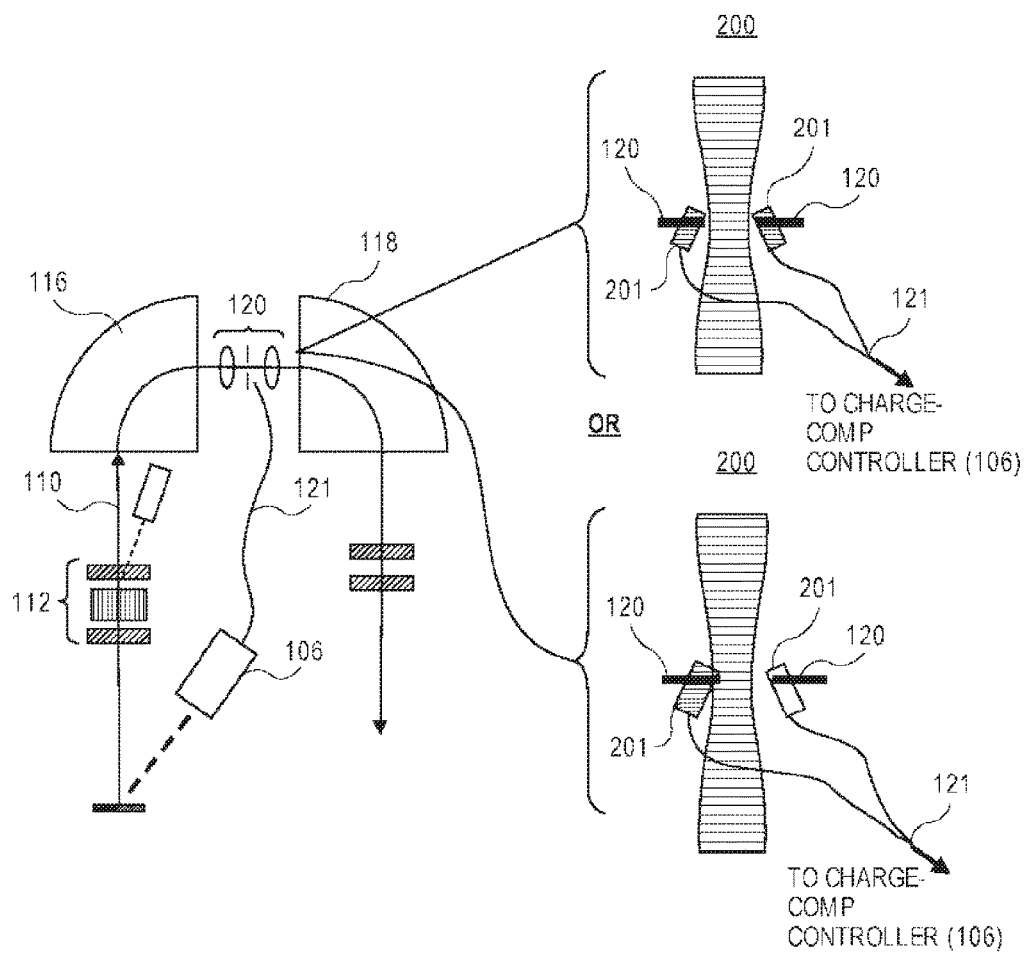
FIG. 2 illustrates schematically charge compensation considerations for a SIMS system, in accordance with an embodiment of the present invention

Additionally, in an embodiment, using a low extraction field makes it easier to deal with sample charging in cases of poor grounding. For example, reducing the field above the sample enables the use of a low-energy electron flood to neutralize the charge. By contrast, in a more typical SIMS design using a strong extraction field, a charge-compensating beam must be run at high energy and precisely steered in order to overcome the deflection by the field and to place the beans accurately at the measurement site, which is a vastly more complicated process. FIG. 2 illustrates schematically charge compensation considerations for a SIMS system. In accordance with an exemplary embodiment, details of a charge compensation system are described, in greater detail below.

Referring to FIG. 2, a portion of the system 100 of FIG. 1 is illustrated on the left-hand side, particularly, the section including the first and second ESAs 116 and 118 and the charge compensation system 106. In a first scenario 200, if an analyzed wafer is at ground potential then the ion beam will nominally be located halfway between the slits 120. The tails of the beam will provide small signals to each of two current detectors 201. In a second scenario 202, if the wafer charges then the ion beam will shift toward one of the slits 120, dependent upon the sign of the charging. The current in the two detectors 201 will change, which may be used to control the charge compensation system 106.

With respect to throughput, the time needed to make a set of measurements on a wafer is a critical factor in the economical application of a measurement technique. In accordance with one or more embodiment of the present invention several secondary ion species are measured in parallel for increased throughput.

To provide context for throughput considerations, common SIMS designs can be grouped into three categories: (1) time-of-flight (TOF), (2) quadrupole detection, and (3) magnetic sector detection. In TOF SIMS, the primary beam is pulsed and the sputtered secondary ion species are sorted according to the time it takes for them to reach a detector. TOF SIMS has the advantage that a wide range of secondary ion species are collected in parallel, but the pulsed nature of the measurement reduces the measurement speed. In the quadrupole approach, the primary beam is applied continuously, but the detector can only measure one ion species at a time (although switching from one species to another can be done quickly). Finally, the third common approach, magnetic sector, separates the ion species according to mass/charge using a combination of electric and magnetic fields. As with the quadrupole system, the primary beam is on continuously. However, in typical magnetic sector systems the spectrometer uses a single detector, which again limits the detection to a single species at a time.

None of the above conventional approaches provide the speed and parallel detection possibly needed for the semiconductor manufacturing environment. By contrast, in accordance with one or more embodiments of the present invention, a magnetic sector spectrograph is used. Like the spectrometer, a magnetic sector spectrograph separates the various mass species by sending the beam through a magnetic field. However, the spectrograph design focuses the different masses along a line, or "focal plane." By placing multiple detectors at various positions along the focal plane, different masses can be measured in parallel. In a particular embodiment, a SIMS system design includes 10 different detectors, enabling measurement of a vast majority of species present in any single semiconductor measurement. It is to be appreciated that fewer than or greater than 10 detectors may be used. It is also to be appreciated that although the entire available range of masses may not be collected in parallel in such an arrangement, as is the case for TOF SIMS, the multi-detector approach is not a detriment since the number of species typically used in any given semiconductor process is limited and the manufacturer usually has a good notion of which species are likely to be present. It should also be noted that the plurality of detectors can be mounted onto translation stages so that their locations along the focal plane, and hence the collected species, can be tailored according to the needs of a specific measurement.

With respect to availability and serviceability, due to the time-critical nature of process control measurements, it is essential that the tool be available for use at the time when a wafer becomes available for measurement. For this reason, it is important that the mean time between failures of the tool is long and the mean time to repair is short. It is further required that the measurement tool is in calibration at all times. Accordingly, the SIMS tool must be capable of checking and updating its calibration automatically In accordance with one or more embodiments herein, several design aspects of a SIMS system are tailored to address such issues concerning availability and serviceability. In one embodiment, to improve the overall stability of the hardware, a monolithic system structure is implemented. For example, every major sub-system, such as the extraction optics, the lower primary column, and the mass spectrometer, may be rigidly mounted to one another. There may be a tradeoff with respect to alignment flexibility, but the advantages include a resulting system that can hold on to an alignment more reliably. In addition, in one embodiment, as depicted in FIG. 1, two turning electrostatic analyzers (ESAs) are added to a secondary path to divert the beam in a direction that allows a several-hundred pound spectrometer magnet to be mounted below a main measurement chamber, near the floor. Such an arrangement improves service access and vibration stability.

In accordance with one or more embodiments herein, to maintain measurement consistency, several internal checks and calibrations are added to a SIMS system. Such internal checks and calibrations may include one or more of (1) a Faraday cup, as depicted in FIG. 1, with a fiducial overlay to verify the current, position, and focus of the primary beam, and/or (2) the ability to read current at several apertures and slits along the secondary path, as depicted in FIG. 1, including the ability to mechanically scan slits to verity the alignment of the beam and monitor any aperture wear.

In an embodiment, a set of internal reference samples is included in a SIMS system. The internal samples can be automatically moved to the measurement site to periodically check various crucial aspects of the beam. These may include layered materials of predetermined thickness to monitor the primary sputtering rates and raster uniformity, patterned boxes of known dimensions to check the raster size and position, and simple chips of various composition to monitor the overall signal strengths. Many of the tests can be performed at a multitude of primary energies and currents. As an example, FIG. 3 illustrates a stage area that includes a Faraday cup and an area for storing calibration standards, in accordance with an embodiment of the present invention.

Figure 3:
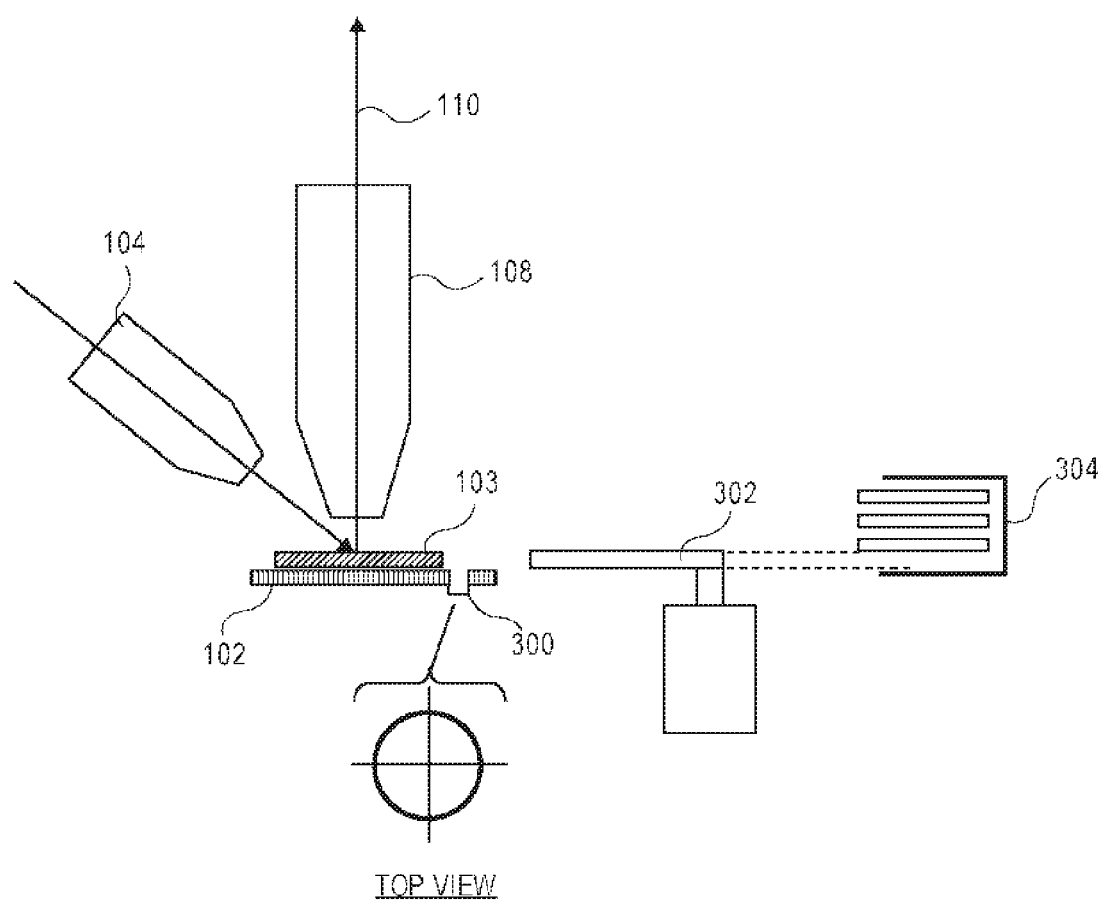
FIG. 3 illustrates a stage area that includes a Faraday cup and an area for storing calibration standards, in accordance with an embodiment of the present invention.

Referring to FIG. 3, a portion of the system 100 of FIG. 1 is illustrated on the left-hand side, particularly, the section including the XY stage 102 and the extraction lens 108. A wafer or sample 103 is situated on the XY stage 102, below the extraction lens 104. The XY stage 300 includes a Faraday cup 300, a top view of which is also shown in FIG. 3. A transfer robot 302 may also be included, along with a "parking lot" for one or more reference wafers such as layered films of known composition and/or film thickness.

In a second aspect, one or more embodiments involve measuring the surface potential of a sample by observing the shift in kinetic energy of emitted charged particles or ions. One or more embodiments involve measuring and controlling the surface potential by using shifts of kinetic energy as a feedback mechanism.

To provide context, secondary ions are generated by removing atoms from a surface, some of which are ionized. The secondary ions are emitted with a range of velocities, or equivalents, a range of kinetic energies. As the ions travel along an optical path, their kinetic enemy at an arbitrary point A will be the sum of the initial kinetic energy (KE), the surface potential of the sample, the local potential at A, and any KE contribution from electrodynamic elements (e.g., buncher, cyclotron, etc.). Determining the KE distribution and comparing it to a distribution from a reference sample with known surface potential provides a measure of the sample potential.

A primary reason to measure surface potential is charging of insulating samples caused by an unequal flow of positive and negative charges to the sample. Secondary ions may be formed by impinging atoms, ions, electrons, or photons onto a surface. Ions and electrons add charge to the surface, while any secondary charged particles emitted from the surface removes charge. If the sample is electrically conducting, it will dissipate any imbalance of charge transport. Insulating overlayers (e.g., which in some cases are laterally patterned) may charge, and the entire sample may charge if it is not electrically connected to an electrode at a stable potential. Furthermore, the surface potential may be measured as material is removed from the surface, possibly exposing variations in sample conductivity or in the emission of charged particles.

In accordance with an embodiment of the present invention, the emitted secondary ions are passed through an electrostatic analyzer so that ions are dispersed in space according to their energies The complete KE distribution is measured by varying the electric field in the ESA, such that the dispersed ion beam travels across an ion detector 120. A change in KE can be measured while intercepting only the low and/or high tails of the energy distribution by using one or two detectors positioned at the tails. In one embodiment, the slope of a tall is measured by slightly modulating the ESA deflecting Held. To preserve the position of the main transmitted beam, the apparatus may have an arrangement of two ESAs with the ion detector(s) 120 there between. In one such embodiment, the second ESA, or the second ESA in conjunction with a matching lens, has an equal and opposite dispersive strength to that of the first ESA.

Particular embodiments of the present invention are directed to measurement and control of the surface potential of a sample by observing the shift in kinetic energy of emitted charged particles and by using shifts of kinetic energy as a feedback mechanism. It is to be appreciated that although exemplary embodiments are described in association with SIMS measurements, embodiments described herein may be applicable to other measurement and metrology techniques and systems.

One or more embodiments are directed to a system of at least one electrostatic analyzer with an energy slit that is equipped with ion current sensors. One or more embodiments are directed to a system and/or approach for measuring energy distribution and energy shift of the total secondary charged particles transported from a sample surface prior to a mass analyzer. One or more embodiments are directed to implementation of an electrostatic analyzer and energy slit feedback system to monitor surface charging. One or more embodiments are directed to utilization of an active control system to adjust the surface potential. In an embodiment, the system of at least one electrostatic analyzer with an energy slit that is equipped with ion current sensors, the system and/or approach for measuring energy distribution and energy shift of the total secondary charged particles transported from a sample surface prior to a mass analyzer, and the electrostatic analyzer and energy slit feedback system implemented to monitor surface charging are used together as a feedback system for surface potential changes.

In an embodiment applicable to SIMS measurements in which the main ion beam is sent through a mass spectrometer, it is often analytically desirable to reject secondary ions which originate near the edge of the eroded area, since these can confound a depth profile. The complete KE distribution may be measured while the main beam is rejected. In one embodiment, the tails of the distribution are measured while the main beam should travel through the mass spectrometer.

Figure 4A:
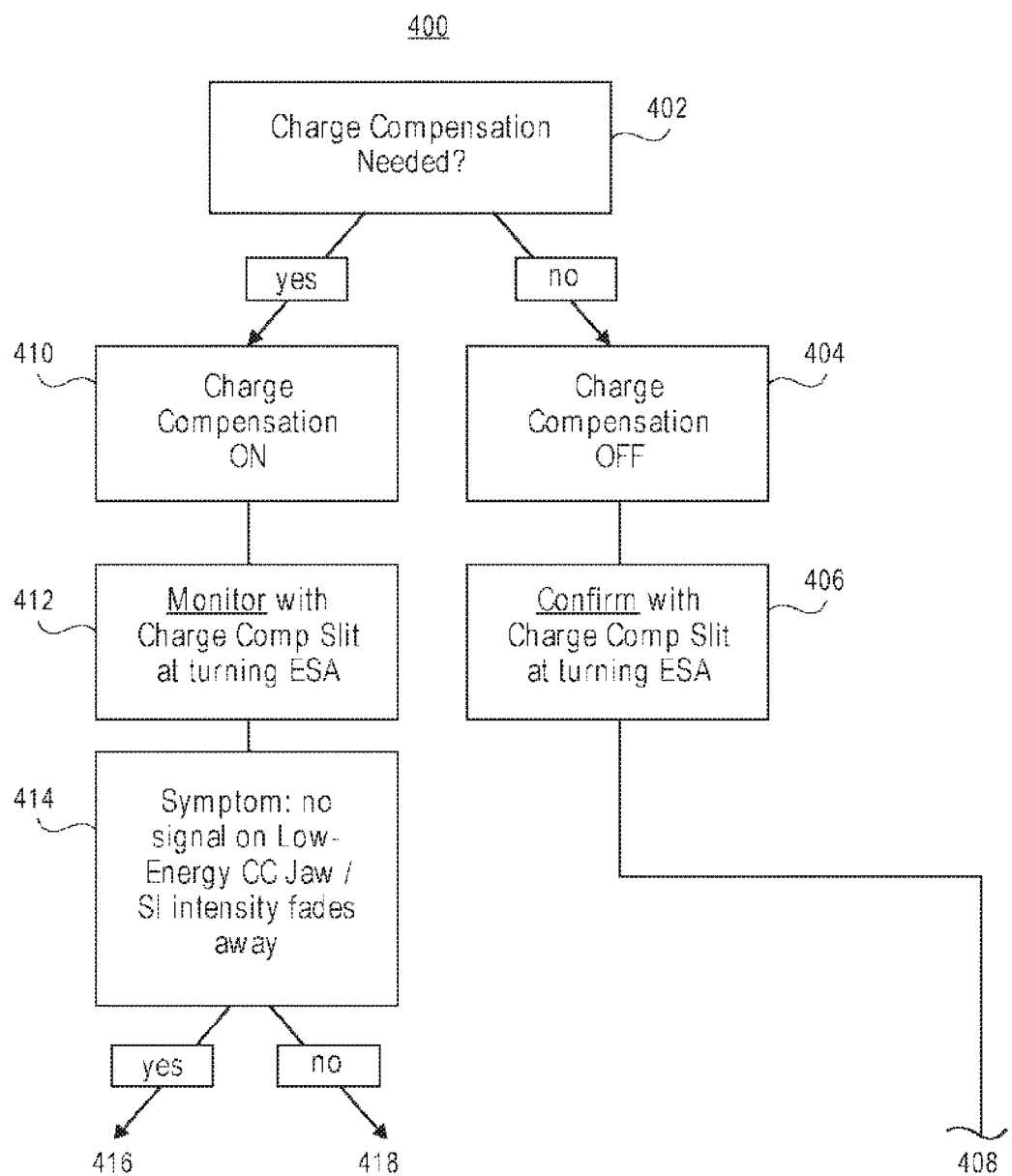
FIGS. 4A and 4B include a schematic representation for the use of a system of electrostatic analyzer and an energy slit equipped with current sensor to monitor and control a charge compensation system, in accordance with an embodiment of the present invention.
Figure 4B:
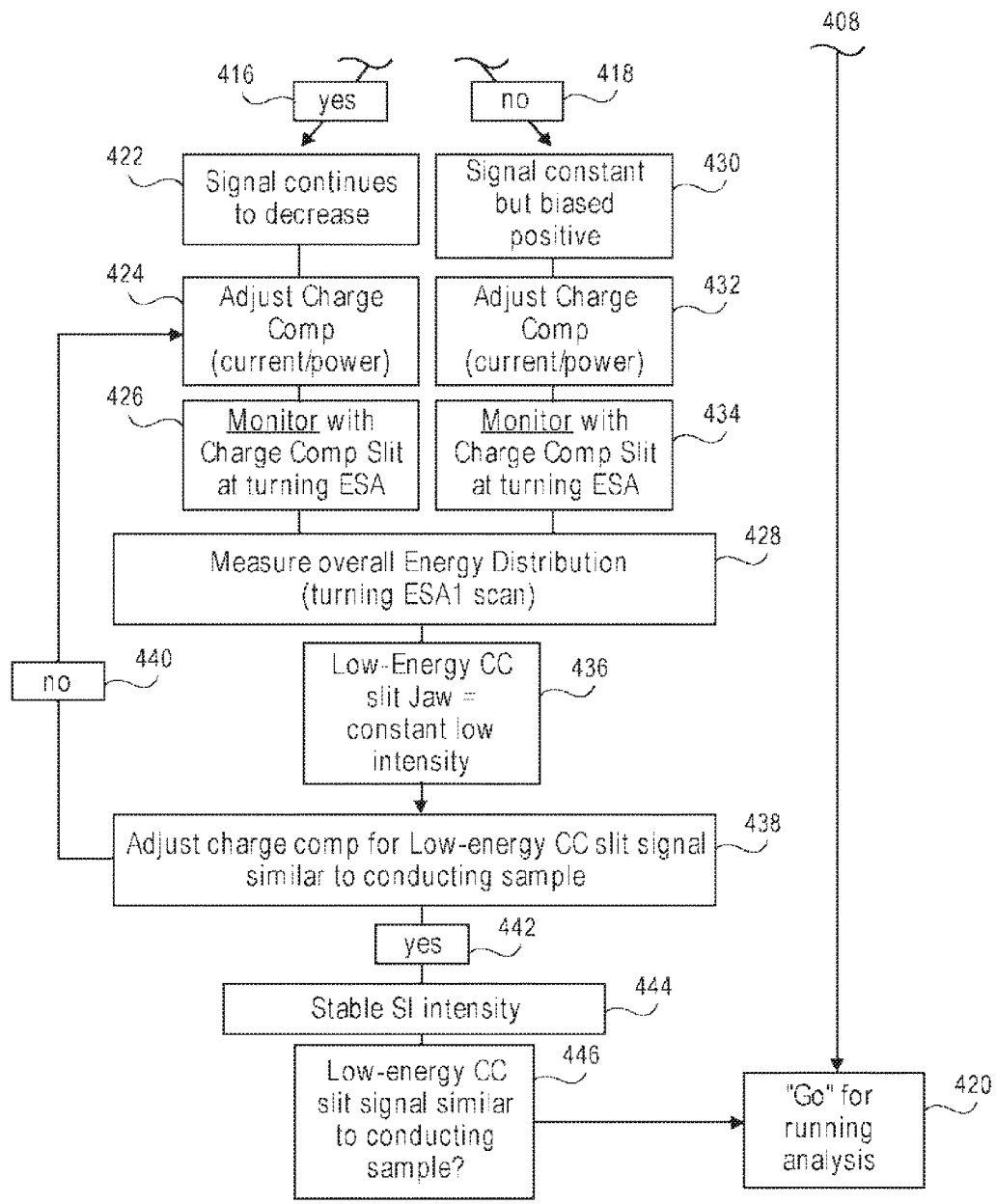

FIGS. 4A and 4B include a schematic representation for the use of a system of electrostatic analyzer and an energy slit equipped with current sensor to monitor and control a charge compensation system, in accordance with an embodiment of the present invention.

Referring to FIG. 4A, a first portion of a flowchart 400 begins with operation 402 to determine if charge compensation is needed, if no charge compensation is needed, then charge compensation is OFF at operation 404. This is confirmed with a charge compensation slit at a turning ESA at operation 406 and progresses to FIG. 4B at 408. If charge compensation is needed, then charge compensation is ON at operation 410. This is monitored with a charge compensation slit at a turning ESA at operation 412. At operation 414, a symptom is determined to see if no signal on low energy charge compensation (CC) Jaw/Si intensity fades away. If yes, the determination progresses to FIG. 4B at 416. If no, the determination progresses to FIG. 4B at 418.

Referring to FIG. 4B, pathway 408 continues to operation 420 which is a "Go" for running the analysis. Pathway 416 continues to operation 422 to determine if the signal continues to decrease. At operation 424, adjustments are made to the charge compensation. At operation 426, monitoring is performed with a charge compensation slit at a turning ESA. At operation 428, overall energy distribution is measured Referring again to FIG. 4B, pathway 418 continues to operation 430 where the signal is constant but biased positive. At operation 432, adjustments are made to the charge compensation. At operation 426, monitoring is performed with a charge compensation slit at a turning ESA. At operation 428, overall energy distribution is measured.

Referring again to FIG. 4B, from operation 428, low energy charge compensation (CC) Jaw/Si intensity is determined at operation 436. At operation 438, adjustments are made for charge compensation for a low-energy CC slit signal and determined if similar to a conducting sample. If no, operation 440 returns to operation 424. If yes, operation 442 leads to operation 444 to determine for stable Si intensify. Then, at operation 446, it is determined if the low-energy CC slit signal is similar to a conducting sample. If so, the flowchart continues to operation 420 which is a "Go" for running the analysis.

Figure 5:
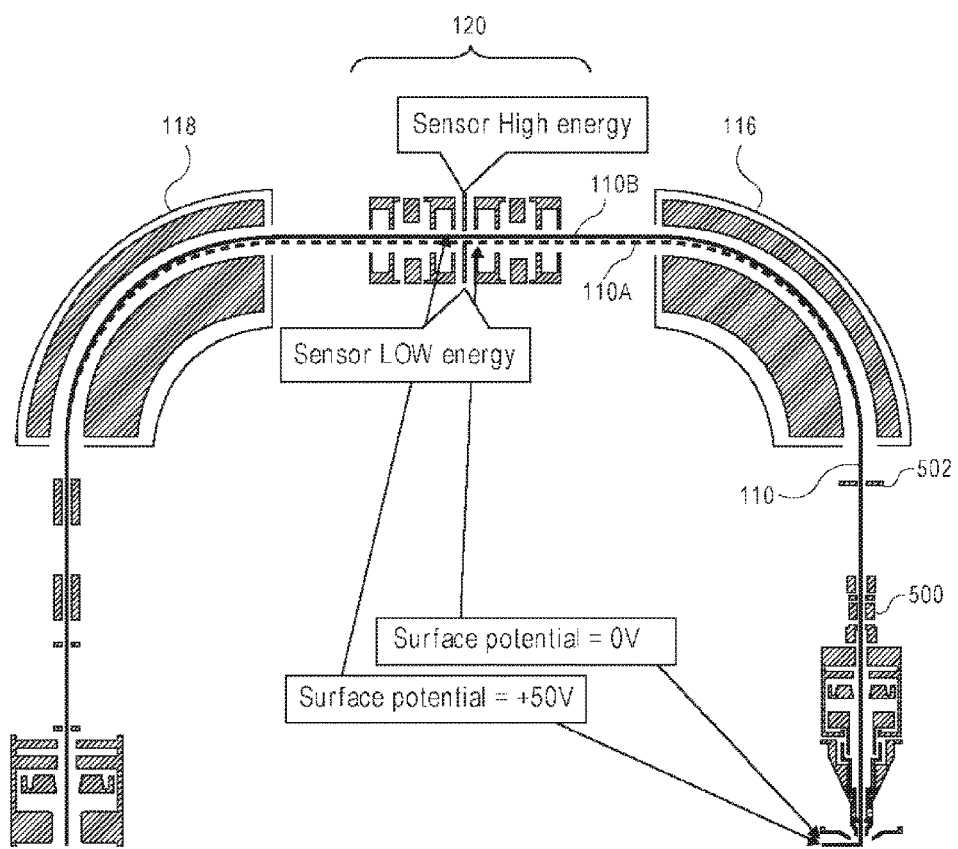
FIG. 5 illustrates a secondary ion beam path through an upper spectrometer and turning electrostatic analyzer (FSA) section, in accordance with an embodiment of the present invention.

FIG. 5 illustrates a secondary ion beam path through an upper spectrometer and turning electrostatic analyzer (ESA) section, in accordance with an embodiment of the present invention.

Referring to FIG. 5, portions of the system 100 of FIG. 1 are shown in greater detail for a particular embodiment The beam 110 in the slit region 120 between ESAs 118 and 116 is split into an inner trace 110A and an outer trace 110B. The inner trace 110A represents a conducting sample (e.g., surface potential 0V). The outer trace 110B represents identical secondary ion distribution with 150V surface potential at the sample. The function of a secondary ion blanker 500 included in the system 100 is to deflect the ions into a total ion current sensor 502.

Referring again to FIG. 5, the effect of changing the sample bias from 0V to 150V for identical secondary ion energy distributions is illustrated. The positive sample bias (or positive charging of the surface) effectively shifts the beam path toward the high-energy sensor of the energy slit of the turning ESA system and increases the measured current on the high energy slit jaw (see –50V sample bias outer trace). At the same time, the low-energy slit jaw will effectively measure no current (see inner trace for 0V bias).

In an embodiment, the high energy slit sensor signal can in turn be used to monitor the effect of a charge neutralization system (for positive secondary ions). For negative secondary ions or electrons, a positive surface potential results in a shift of the energy distribution toward the low-energy slit sensor and may in the extreme effectively suppress secondary ion emission from the sample surface altogether (as the negative charged particles are attracted to the positive sample potential).

Figure 6:
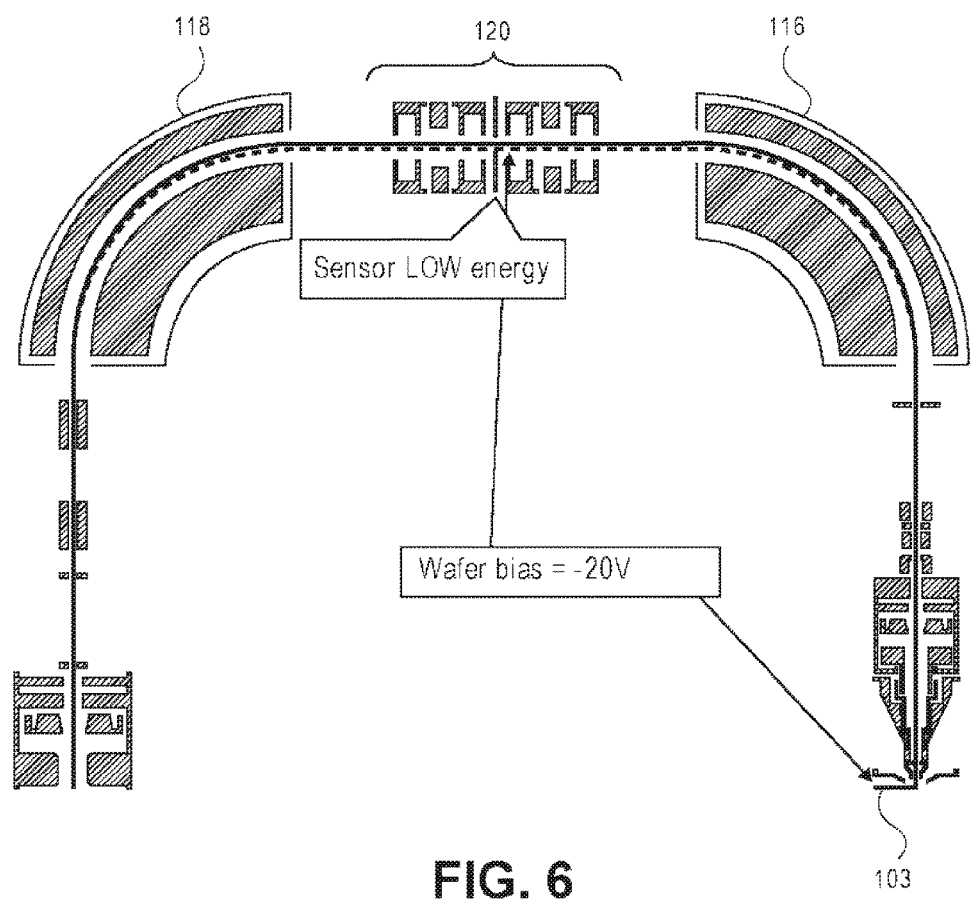
FIG. 6 illustrates a secondary ion beam path for positive ions through an upper spectrometer and turning electrostatic analyzer (ESA) section, in accordance with an embodiment of the present invention.

FIG. 6 illustrates a secondary ion beam path for positive ions through an upper spectrometer and turning electrostatic analyzer (ESA) section, in accordance with an embodiment of the present invention.

Referring to FIG. 6, portions of the system 100 of FIG. 1 are shown in greater detail for a particular embodiment, with a sample location 103 depicted. The trajectory trace indicates surface charging toward negative (e.g., –20V) surface potential. That is, positive secondary ions appear to shift toward lower secondary ion energy. Secondary ions are cut off at the low energy slit sensor.

In an embodiment, if the sample surface accumulates a negative potential, positive secondary ions will shift toward apparent lower secondary ion energy. This shift may occur when the overall sample potential is changes from positive to less positive potential. The cause of such shifts may be due to one or more of the following factors: (a) an intentional sample bias used to reject low-energy secondary ions, (b) if a constant positive surface potential is induced on a semi-insulating sample and the sample is irradiated with higher energy electrons that cause a net negative surface charge, and/or (c) the overall sample bias is set to a more negative potential for a conducting sample to reject low-energy secondary ions from the measurement.

Figure 7:
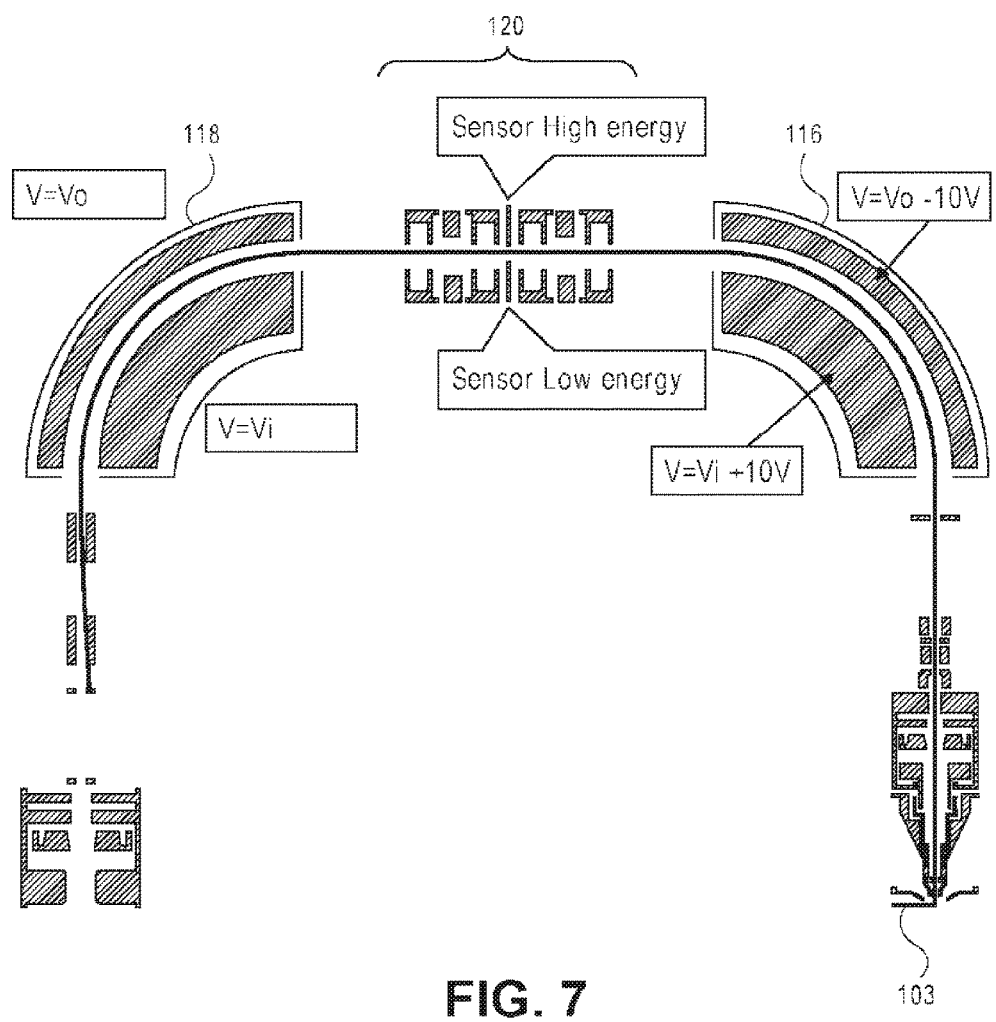
FIG. 7 illustrates an energy distribution scan toward high energy, using the low and high energy current sensors following turning ESA 116 as feedback which changes the mean pass energy of the electrostatic analyzer, in accordance with an embodiment of the present invention.

FIG. 7 illustrates an energy distribution scan toward high energy, using the low and high energy current sensors following turning ESA 116 as feedback which changes the mean pass energy of the electrostatic analyzer, in accordance with an embodiment of the present invention.

Referring to FIG. 7, portions of the system 100 of FIG. 1 are shown in greater detail for a particular embodiment, with a sample location 103 depicted. The approach involves turning ESA scan on ESA 116 only (outer ESA Vo–10V, inner Vi–10V) while ESA 118 is at nominal voltages. The system will not transmit the secondary ions to the mass analyzer since ESA 118 is still tuned to the nominal pass energy.

FIGS. 8A, 8B, 8C, and 8D include a schematic illustration 800 for measuring the secondary ion energy distribution using the electrostatic turning ESA 116, as well as the high- and low-energy slit sensors described in association with FIG. 7, in accordance with an embodiment of the present invention. In an embodiment, a same or similar experimental setup can be used for monitoring the effectiveness of a charge compensation system as described in association with FIGS. 4A and 4B. The implementation may be in conjunction with additional features to control or adjust the surface potential of the sample as described in the above approaches for adjusting the surface potential.

Figure 8A:
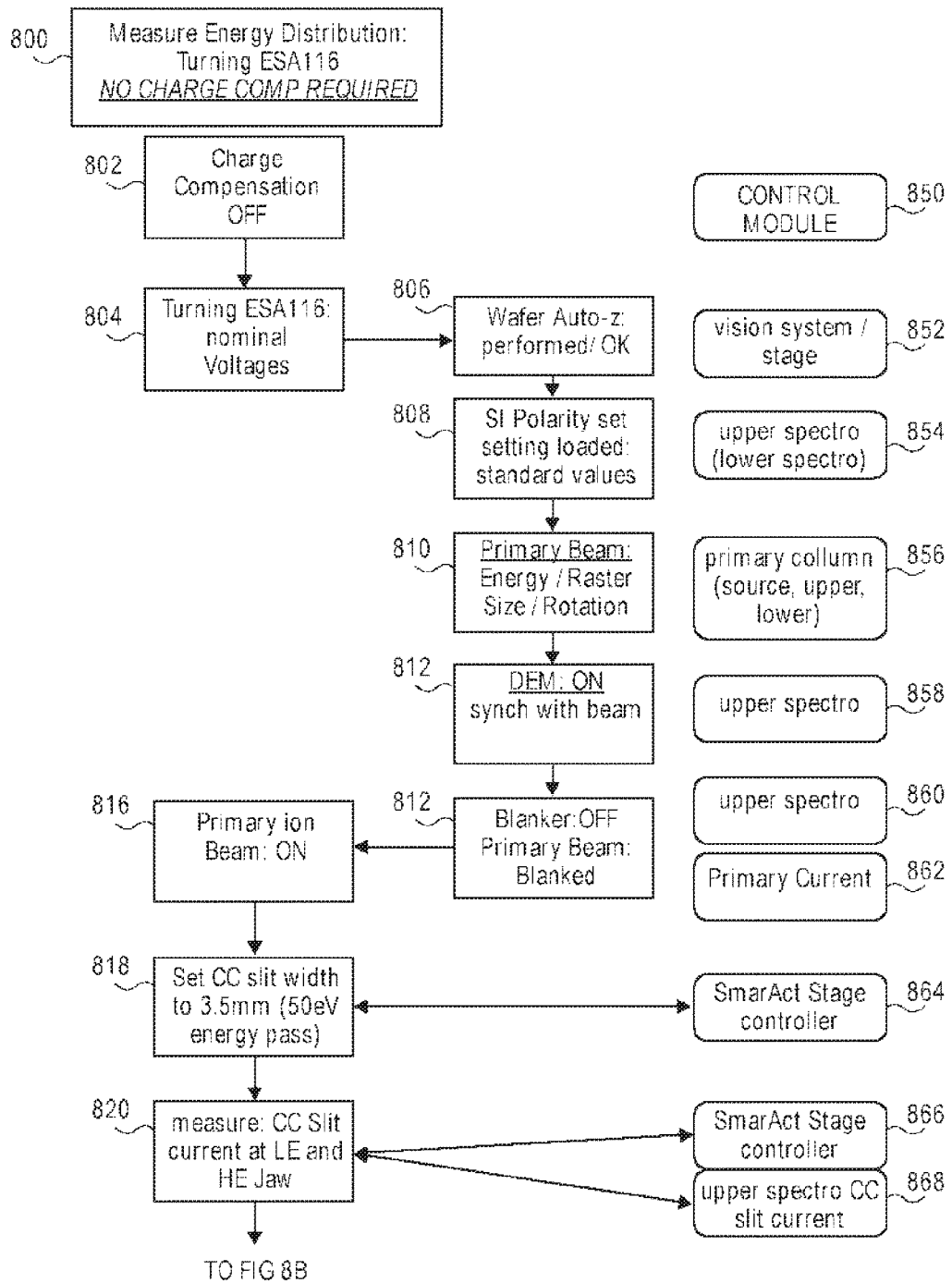
FIGS. 8A, 8B, 8C, and 8D include a schematic illustration for measuring the secondary ion energy distribution using the electrostatic turning ESA 116, as well as the high- and low-energy slit sensors described in association with FIG. 7, in accordance with an embodiment of the present invention.

Referring to FIG. 8A, the energy distribution scan is on the charge compensation (CC) slit 120 after turning ESA 116. In an exemplary embodiment, the sample is silicon or SiGe and is well grounded. This setting is used for charge compensation reference as well. Energy adjustment is to be accomplished via e-beam current/energy to move ion energy back toward the slit detector. At operation 802, charge compensation is OFF. At operation 804, turning ESA 116 is at nominal voltages. At operation 806, a wafer auto-z is performed and checked for OK. At a corresponding control module 850, a vision system/stage operation 852 is used for performing operation 806. At operation 808, a silicon polarity set is loaded at standard setting values. At the corresponding control module 850, an upper spectra (or lower spectro) operation 854 is used for performing operation 808. At operation 810, a primary beam energy-raster size/rotation adjustment is performed. At the corresponding control module 850, a primary column operation 856 is used for performing operation 810. At operation 812, a synch with beam is performed. At the corresponding control module 850, an upper spectro operation 858 is used for performing operation 812. At operations 814 and 816, the primary beam is blanked and then set ON, respectively. At the corresponding control module 850, an upper spectro operation 860 and a primary current operation 862 is used for performing operations 814 and 816, respectively. At operation 818, charge compensation slit width is set (e.g., to 3.5 mm of a 50 eV energy pass). At the corresponding control module 850, a smart stage controller operation 864 is used for performing operation 818. At operation 820, charge compensation (CC) is determined by measuring slit current. At the corresponding control module 850, a smart stage controller operation 866 and an upper spectro charge compensation slit current operation 868 are used for performing operation 820. Flow from operation 820 then continues at FIG. 8B.

Figure 8B:
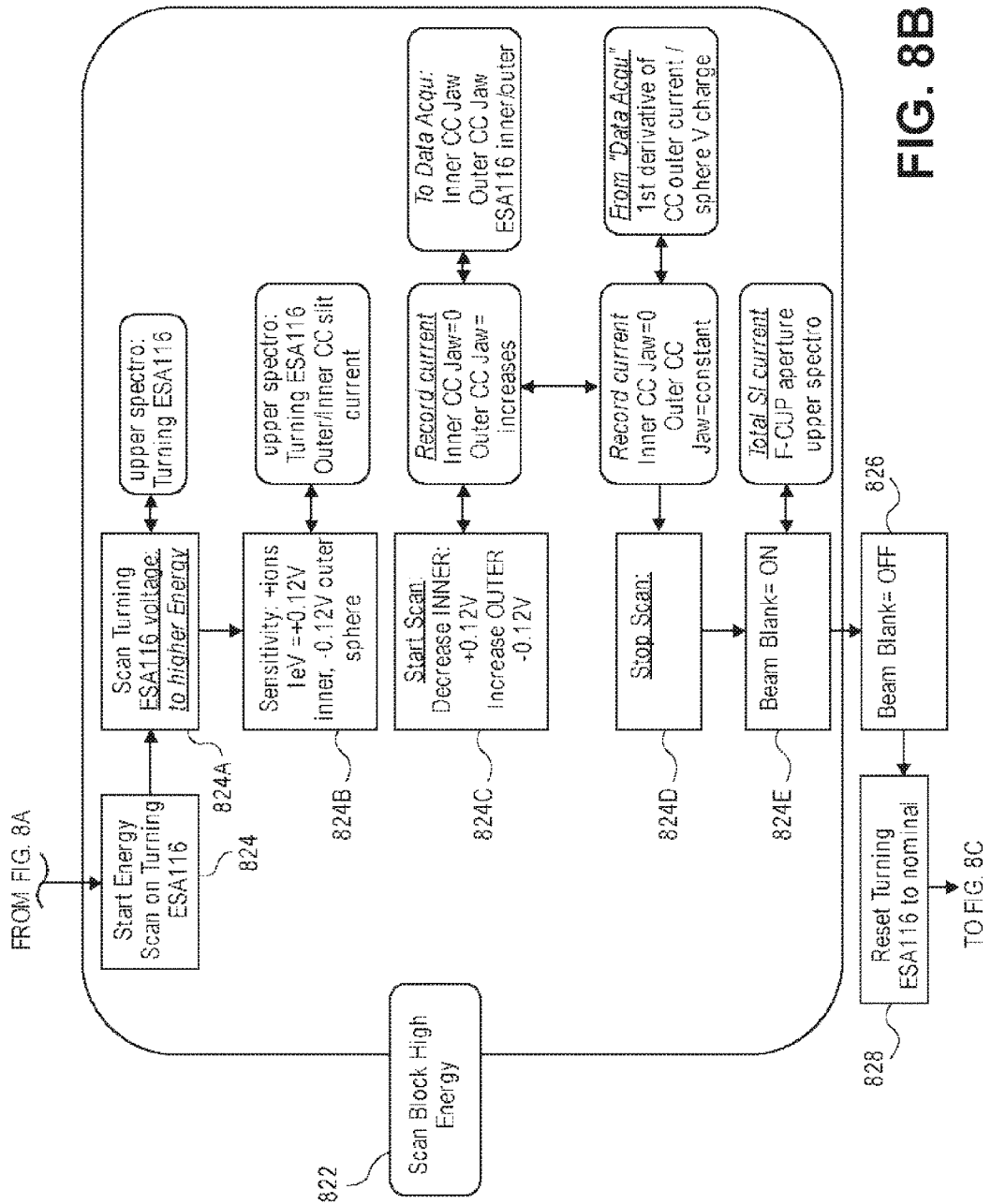

Referring to FIG. 8B, from operation 820, a scan block high energy operation 822 is performed, which marks a start energy scan operation 824 at ESA 116, which continues through operations 824A-824E as depicted in FIG. 8B. The charge compensation program ends operation 822 at operation 826 with the beam blank setting at OFF. The turning ESA 116 is then set to nominal at operation 828. Flow from operation 828 then continues at FIG. 8C.

Figure 8C:
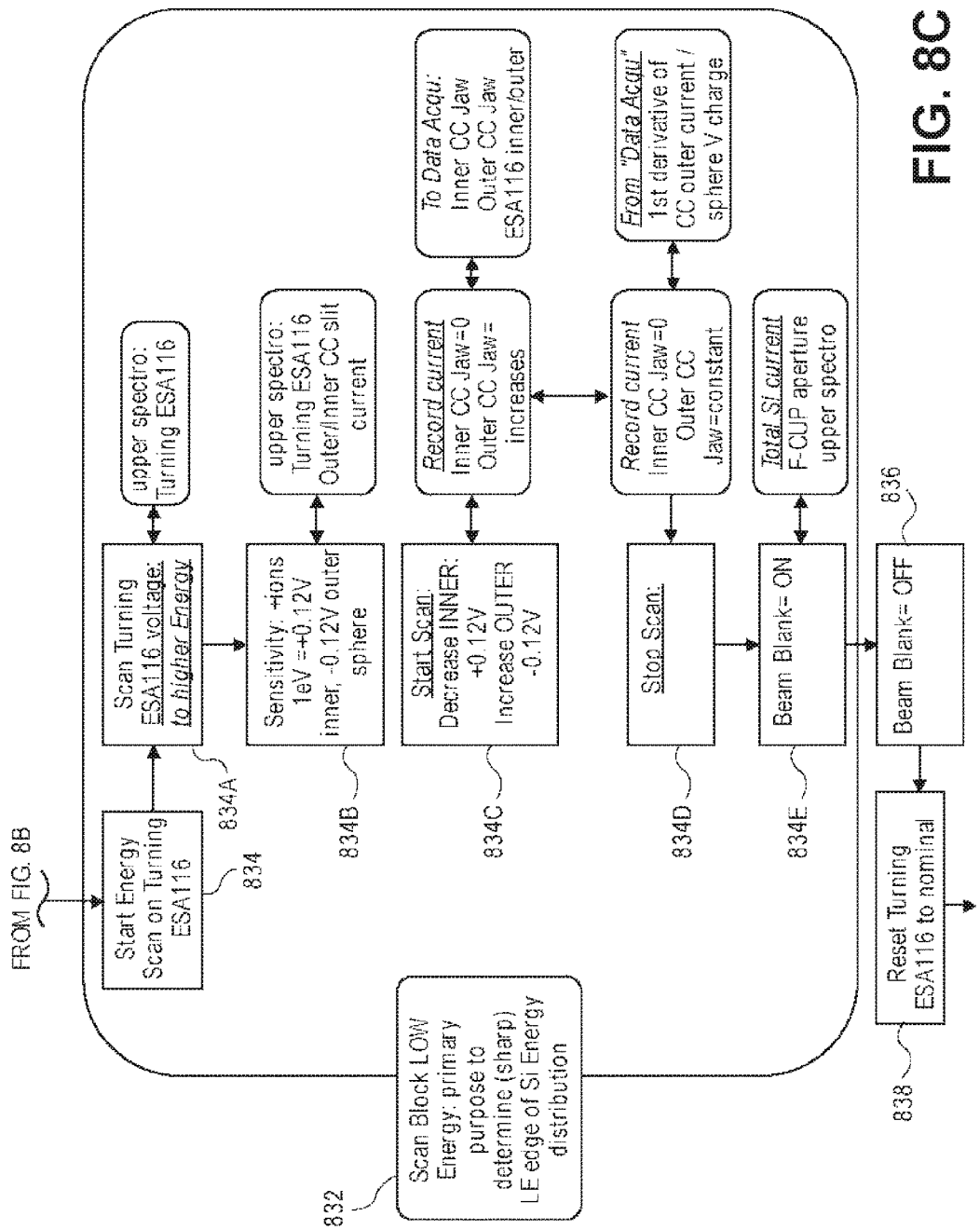

Referring to FIG. 8C, from operation 828, a reverse turning ESA 116 scan operation 830 is performed. A scan block low energy operation 832 is then performed, which marks a start energy scan operation 834 at ESA 116, which continues through operations 834A-834E as depicted in FIG. 8C. The charge compensation program ends operation 832 at operation 836 with the secondary beam blank setting at OFF. The turning ESA 116 is then set to nominal at operation 838.

Figure 8D:
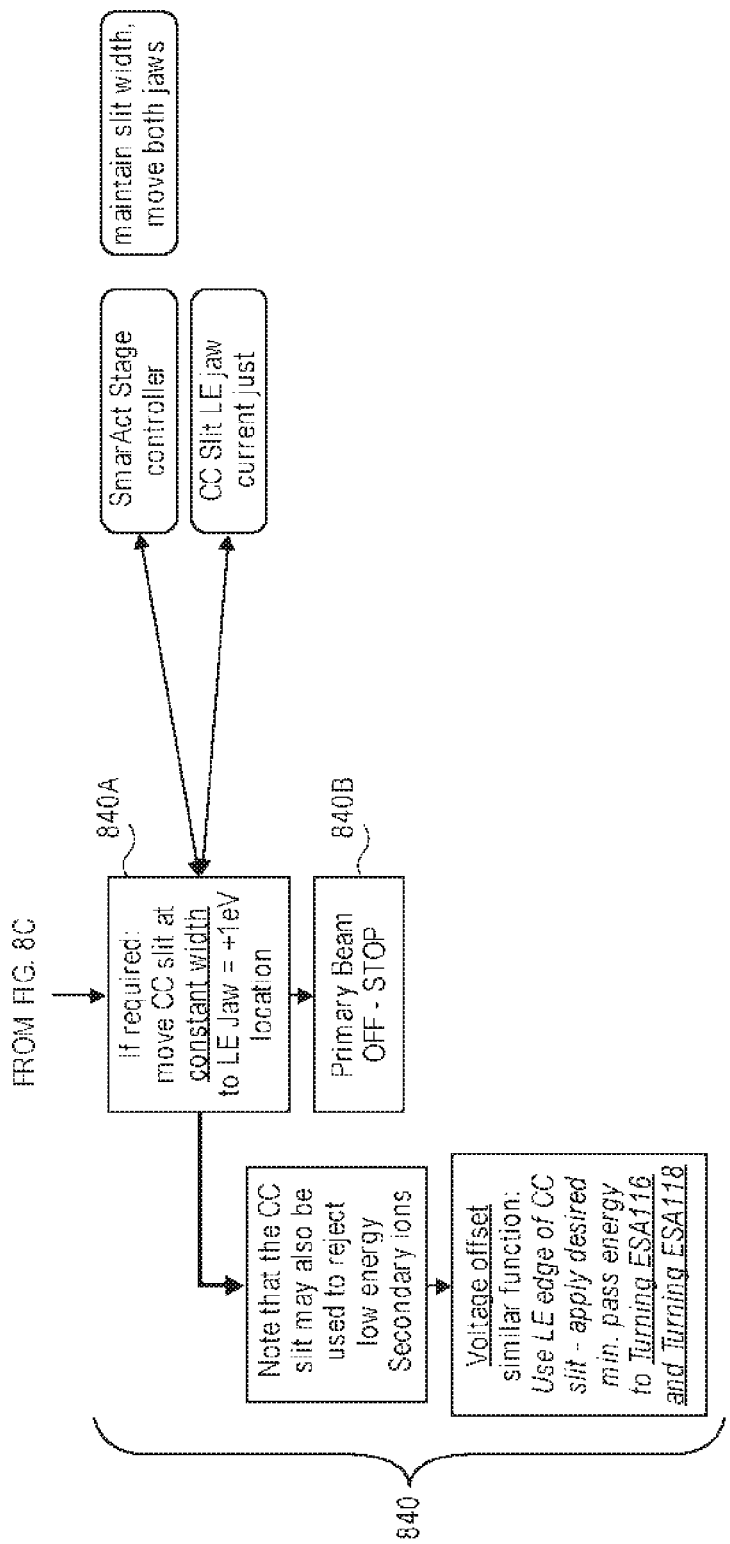

Referring to FIG. 8D, if further compensation is however required, further determinations may be performed at operation 840. For example, at operation 840A, if required, the charge compensation (CC) slit is moved at constant width for a target voltage. It is to be appreciated that, in one embodiment, the charge compensation slit may also be used to reject low energy Secondary ions. It is also to be appreciated that a voltage offset may be applied to enable passage of a minimum pass energy to ESA 116 and ESA 118. At operation 840B, the primary beam is stopped (OFF position).

Figure 9:
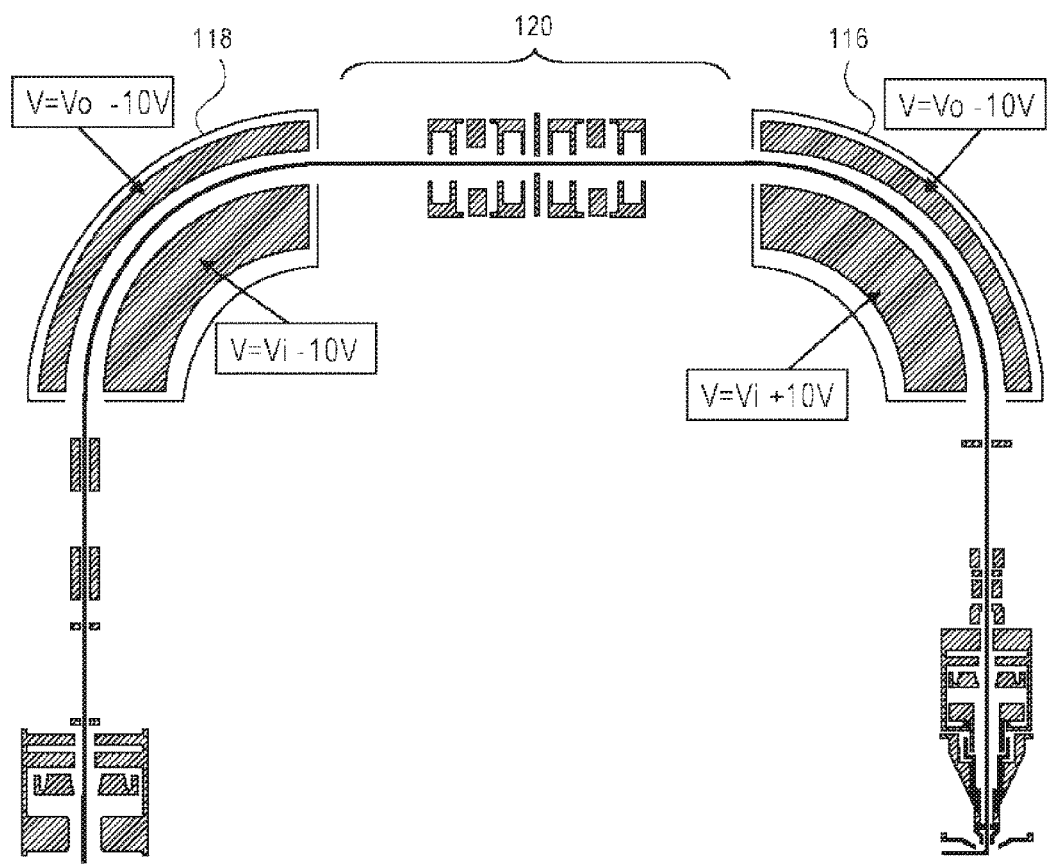
FIG. 9 illustrates an energy distribution scan involving turning ESA scan on ESA 116 and ESA 118 at a same voltage, in accordance with an embodiment of the present invention.

FIG. 9 illustrates an energy distribution scan involving turning ESA scan on ESA 116 and ESA 118 at a same voltage, in accordance with an embodiment of the present invention. Referring to FIG. 9, portions of the system 100 of FIG. 1 are shown in greater detail for a particular embodiment. The approach involves setting the outer portions of ESAs 116 and 118 at Vo−10V. The inner portions of ESAs 116 and 118 are set at Vi−10V.

Thus, embodiments include approaches to controlling the surface potential of a sample. In an embodiment, the potential at the sample surface can be controlled using one or more of (1) adjusting the bias voltage of the sample substrate (described in greater detail below, in association with FIG. 10), (2) directing a beam of electrons at the surface and varying the current delivered to the sample surface (described in greater detail below, in association with FIG. 11), (3) directing a beam of electrons at the surface and varying the impact energy of the electrons, such that the secondary electrons coefficient is either greater than 1 (driving the sample potential more positive), or less than one (driving the sample potential more negative), (4) a combination of (2) and (3) such that the net charge flux delivered by the electron beam can be of either polarity and variable in intensity, (5) directing a variable intensity of photons to the sample surface such that charge carriers are generated in the sample, varying its conductivity (described in greater detail below, in association with FIG. 12), (6) directing a variable intensity of photons to the sample surface such that photoelectrons are emitted from the sample, driving the sample potential more positive, (7) directing a variable intensity of photons away from the sample surface onto a material of high secondary electron coefficient and flooding the sample surface with low-energy electrons, thus driving the sample potential more negative (described in greater detail below, in association with FIGS. 13A and 13B), and/or (8) the approach of (7), while applying a positive or negative potential to the electron emitting material to control the flux and energy of electrons striking the sample surface.

Figure 10:
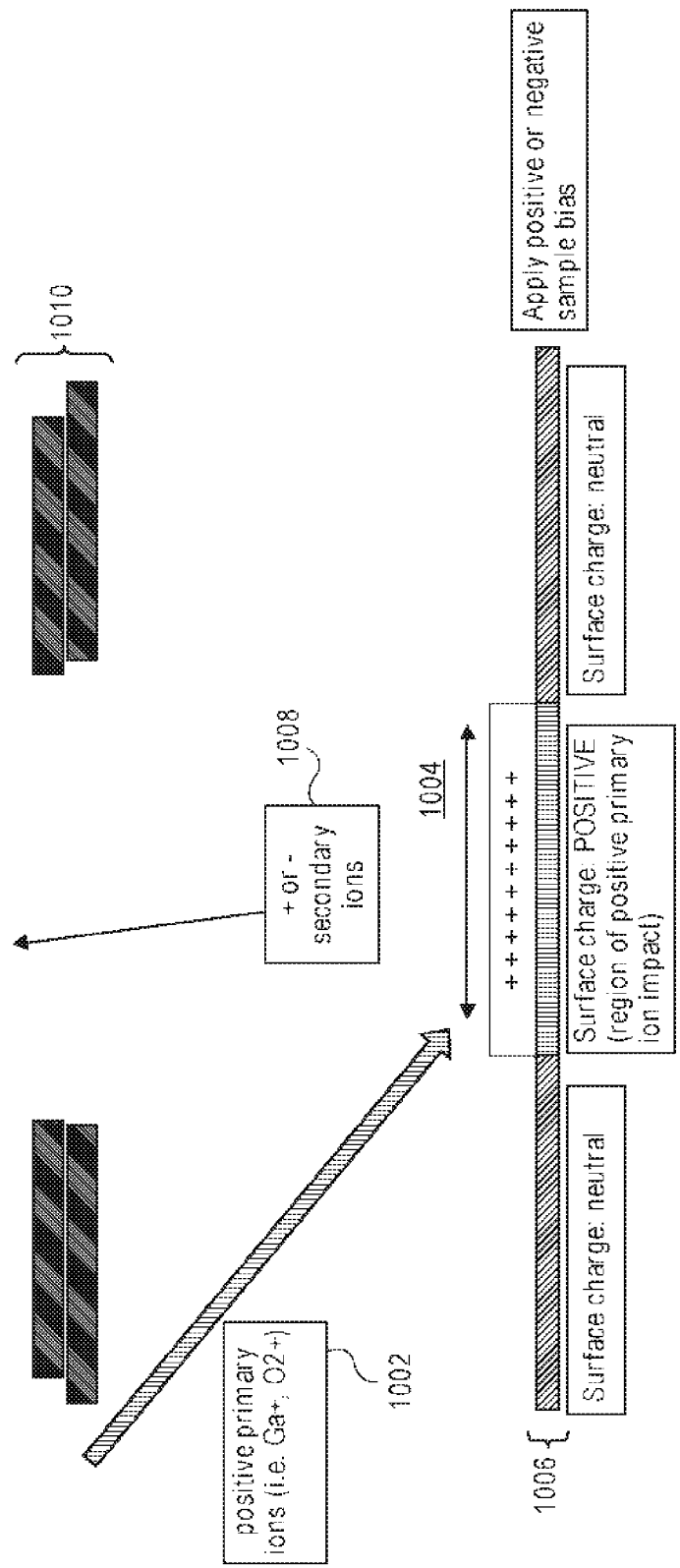
FIG. 10 is a schematic illustrating a positive potential on the sample due to surface charging, in accordance with an embodiment of the present invention.

FIG. 10 is a schematic illustrating a positive potential on the sample due to surface charging, in accordance with an embodiment of the present invention.

Referring to FIG. 10, a positive primary ion beam 1002 is directed at a portion 1004 of a sample 1006. Secondary ions 1008 are generated and collected at an extraction module 1010. The sample potential of the sample 1006 (and in particular the portion 1004 of the sample 1006) can be adjusted, e.g., by adjusting the bias voltage of the sample substrate.

Figure 11:
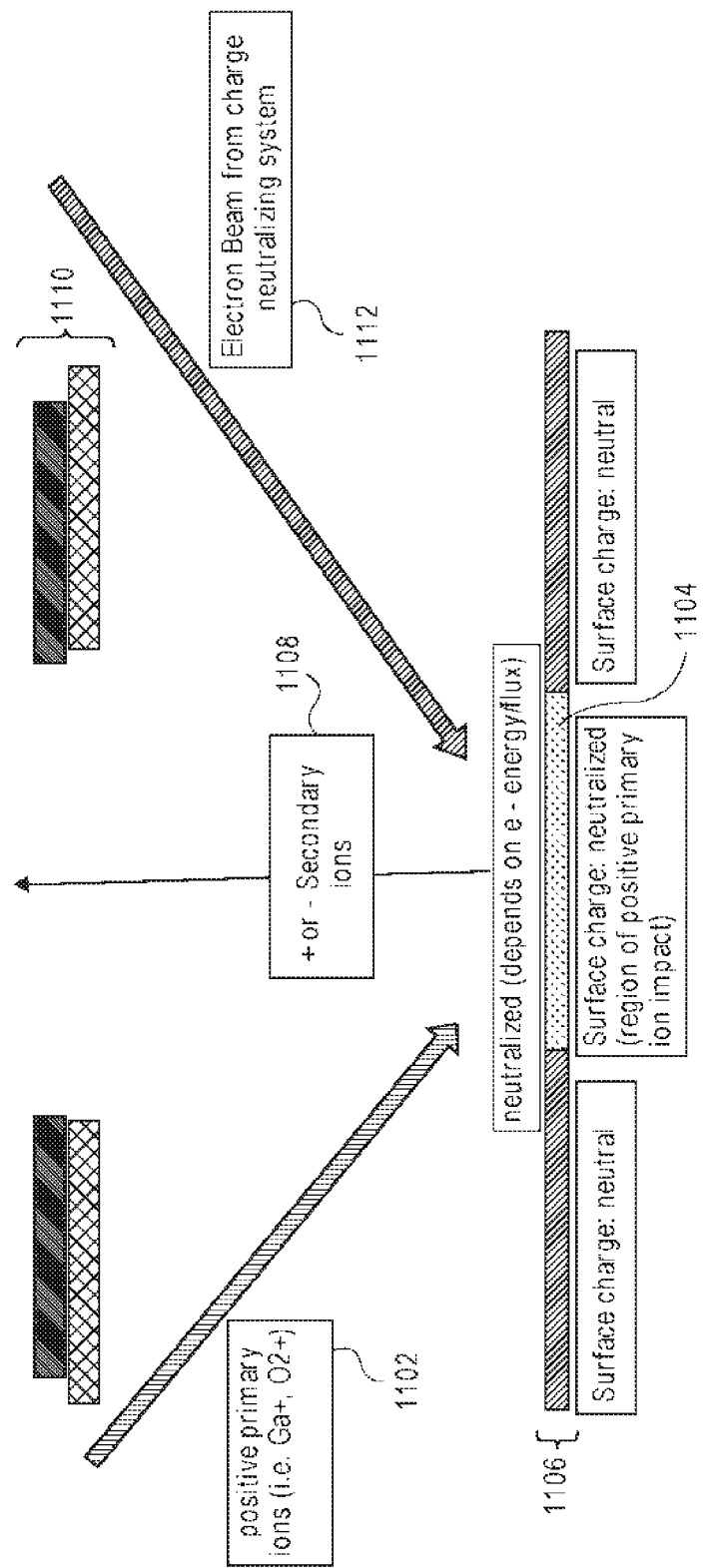
FIG. 11 is a schematic illustrating electron beam based charge neutralization and control, in accordance with an embodiment of the present invention.

FIG. 11 is a schematic illustrating electron beam based charge neutralization and control, in accordance with an embodiment of the present invention.

Referring to FIG. 11, a positive primary ion beam 1102 is directed at a portion 1104 of a sample 1106. Secondary ions 1108 are generated and collected at an extraction module 1110. A beam of electrons 1112 is directed at the surface of 1104. Meanwhile, the current delivered to the sample surface is varied.

Figure 12:
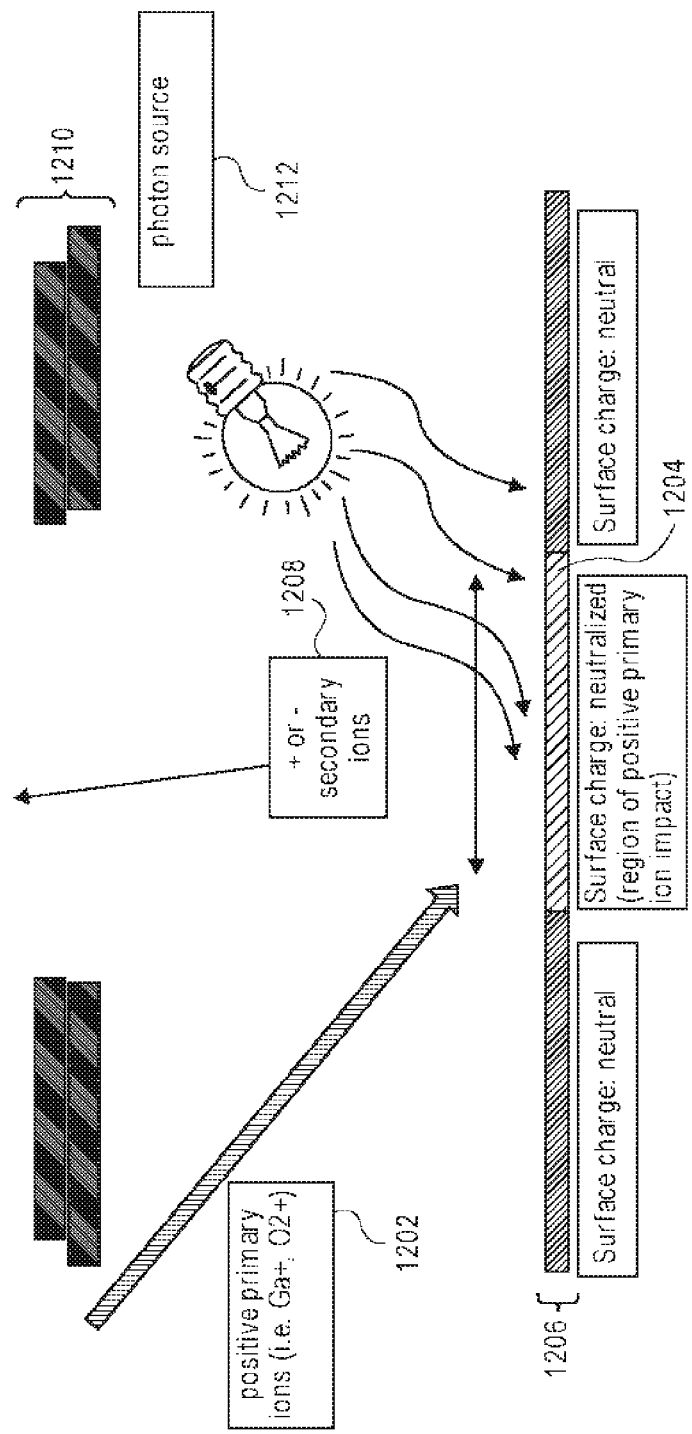
FIG. 12 is a schematic illustrating photo conductivity of the sample using a variable intensity photon source, in accordance with an embodiment of the present invention.

FIG. 12 is a schematic illustrating photo conductivity of the sample using a variable intensity photon source, in accordance with an embodiment of the present invention.

Referring to FIG. 12, a positive primary ion beam 1202 is directed at a portion 1204 of a sample 1206. Secondary ions 1208 are generated and collected at an extraction module 1210. A variable intensity of photons 1212 is directed to the surface of 1204 such that charge carriers are generated in the sample, varying its conductivity.

Figure 13A:
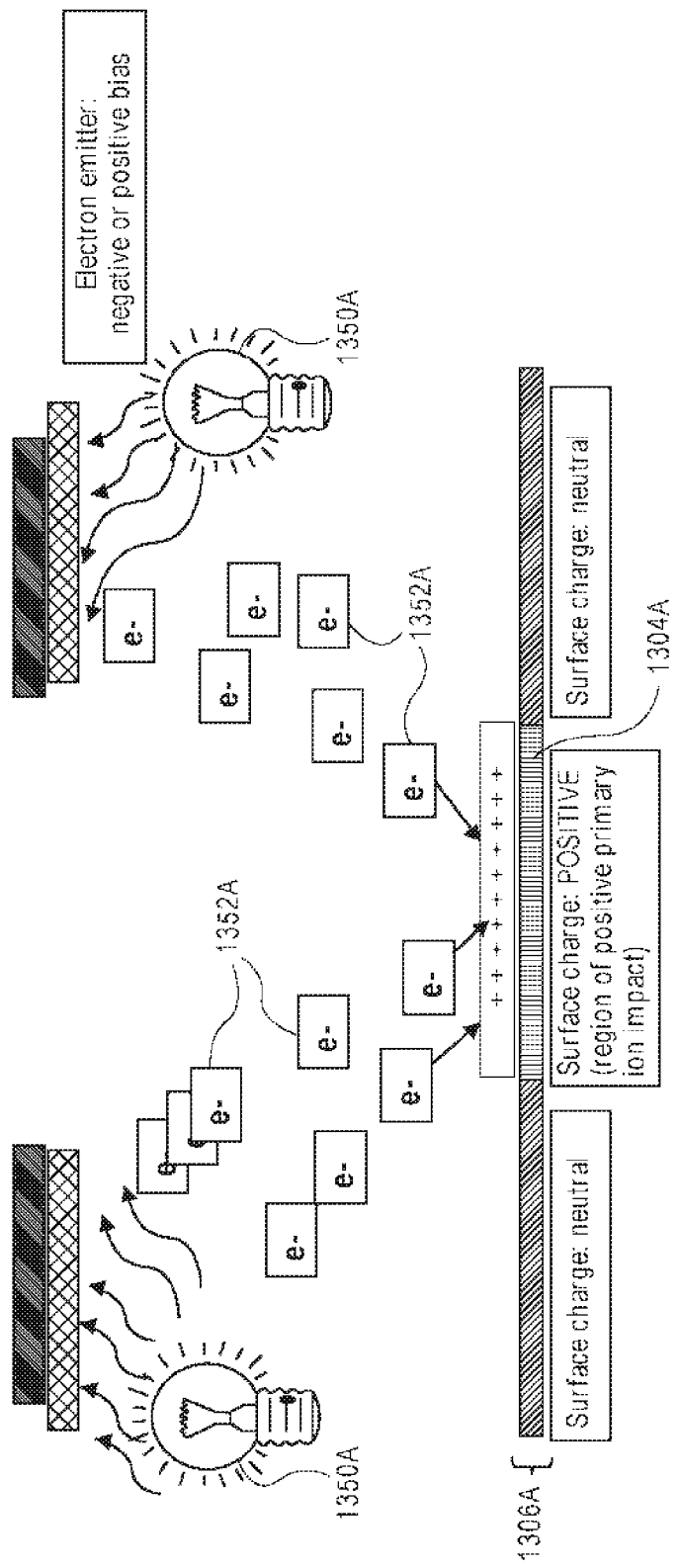
FIG. 13A is a schematic illustrating charge neutralization by use of an electron emitting material away from the sample, in accordance with an embodiment of the present invention.

FIG. 13A is a schematic illustrating charge neutralization by use of an electron emitting material away from the sample, in accordance with an embodiment of the present invention. Referring to FIG. 13A, a region 1304A of a sample 1306A is charged positive. Electron emitters 1350A are included in the system. Low-energy electrons 1352A are attracted by the positive surface potential of the region 1304A of the sample 1306A.

Figure 13B:
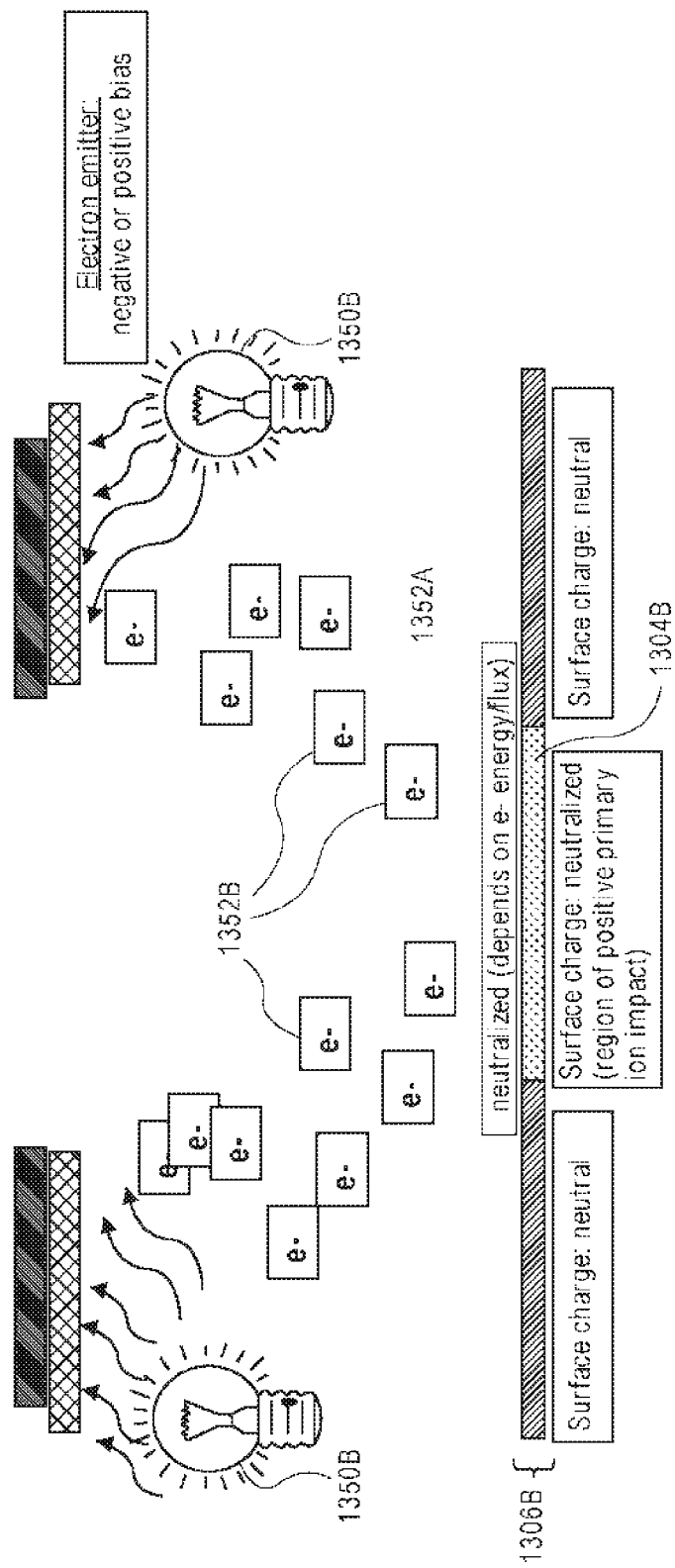
FIG. 13B is a schematic illustrating effective charge neutralization if the electron flux exceeds the primary ion induced positive surface charge, in accordance with an embodiment of the present invention.

FIG. 13B is a schematic illustrating effective charge neutralization if the electron flux exceeds the primary ion induced positive surface charge, in accordance with an embodiment of the present invention. Referring to FIG. 13B, a region 1304B of a sample 1306B is charge neutral. Electron emitters 1350B are included in the system. Net surface potential is equal to max electron energy of the electrons 1352B. Referring to FIGS. 13A and 13B collectively, a variable intensity of photons is directed away from the sample surface onto a material of high secondary electron coefficient and the sample surface is flooded with low-energy electrons, thus driving the sample potential more negative.

In a third aspect, embodiments of the present invention are directed to methods for determining wafer backside contact resistance using multiple capacitive height sensors.

To provide context, in metrology equipment for semiconductor wafers it is common to use either charged particle (electrons/ions) beams as a primary exciting source, or measure the properties of charged particles that are emitted from the wafer, or both. Charging of the wafer can cause either errors in measuring the properties of the emitted particles or cause the primary charged particle to be deflected into neighboring regions causing damage to these areas. To keep the wafer from charging it is common to make contact to the backside of the wafer with a conductive electrode. However, in some instances, due to contamination on the electrode or insulating films on the back of the wafer, there is a high resistance between the electrode and the wafer. It may be desirable to measure the backside contact resistance in order to be assured that it is safe to apply an associated primary ion or electron beam to the sample.

In accordance with an embodiment of the present invention, approaches for measuring a contact resistance by using multiple capacitive height sensors are described. To exemplify the concepts described herein, a case of a single sensor being used to measure the height to a well-grounded wafer is first considered. The sensor includes a parallel plate electrode that is within sensing distance to the wafer. The structure forms a parallel plate capacitor where one plate is the sensor and the other is the wafer. If an AC voltage is applied to the sensor, then current flows across the gap between the plates. The amount of current that flows across the gap is determined by the voltage, the area of the plates, the material that separates the plates, and the distance between the plates.

The relevant equations to describe the current are: $i_{ac}$ x*C*V, where $i_{ac}$ ac current (in amps), C=capacitance (in farads), V=voltage, and x is a constant that depends only on the ac frequency. Capacitance (C) in turn is defined as C=K*E0*A/D, where C=capacitance (in farads), K the dielectric constant of the material between the plates (e.g., Air 1.0), E0 permittivity of free space (a constant), A area of the plates (in square meters), D distance between the plates (in meters). Thus, if the area of the sensor is maintained as constant, the distance (D) is proportional to the voltage (V) divided by the current ($i_{ac}$). For an AC voltage, this is directly proportional to the impedance of the circuit.

The control electronic for the sensor can be implemented several ways. For example, some capacitive sensors hold the current constant and allow the voltage to vary. These are called constant current capacitive sensors. Other capacitive sensors hold the voltage constant and allow the current to vary. These are constant voltage designs. There is no inherent advantage of one design over the other.

The above description assumes that the wafer is well grounded to the measurement electronics such that the impedance that is measured is due to the sensor to wafer gap. If the wafer is not well grounded, then the sum of the impedance due to the sensor to wafer gap and the impedance of the wafer to ground is what is measured. This, unfortunately, results in a distance being reported that is the sum of the wafer to sensor gap and the error from the wafer impedance. Approaches for using a second sensor or compensating electrode to minimize the wafer to ground current have been described for reducing the error in the distance measurement. The general idea is to feed the second electrode with an AC voltage that is amplitude and/or phase shifted version of the drive signal that is fed to the main sensor electrode. When the net current of the two electrodes is zero then the value from the main electrode is an accurate measure of the gap distance.

Figure 14:
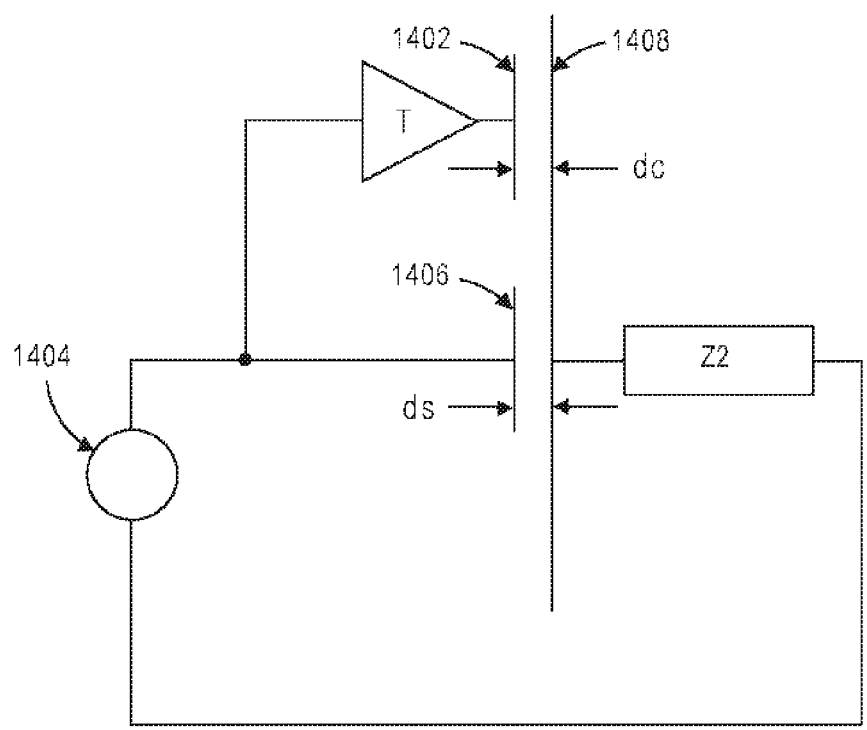
FIG. 14 illustrates schematically some of the parameters involved in using a compensating electrode to determine gap distance.

FIG. 14 illustrates schematically some of the parameters involved in using a compensating electrode to determine gap distance. Referring to FIG. 14, a compensating electrode 1402 is shown as coupled to a sensor signal generator 1404. A sensor 1406 is coupled to the sensor signal generator 1404. The arrangement in FIG. 14 shows the relationship of the compensating electrode 1402, the sensor signal generator 1404, and the sensor 1406 to a target 1408.

It is to be appreciated that, in accordance with an embodiment of the present invention, it is of interest to further determine the value of the signal being driven to the compensating electrode. The value is a measure of the wafer impedance to ground. By determining the signal and calibrating it with known reference impedance standards added between ground and a conductive wafer, the signal can be calibrated such that an unknown contact resistance can be determined.

In accordance with an embodiment of the present invention, there are several options for performing a measurement of a compensating electrode signal. In a first embodiment, an approach involving drive of a compensating electrode with a 180 degree shifted version of the main electrode signal. The amplitude is adjusted until the net current is zero (or until the distance measured by the main electrode is minimized). The amplitude of the voltage on the compensating electrode can then be calibrated to the impedance. In a second embodiment, the distance indicated by the main sensor is measured as the compensating electrode is being driven by a phase shifted version of the main signal. The distances are plotted for a number of different phase angles and a curve fitting algorithm is used to determine the phase angle for the minimum distance. The obtained phase angle is then calibrated to the impedance. In a third embodiment, the distance of the compensating electrode to the wafer or the exposed area of the compensating electrode is varied. The distance on the main electrode is measured to determine the minimum and, thus, a value is obtained that can be calibrated to the impedance.

Embodiments of the present invention may be provided as a computer program product, or software, that may include a machine-readable medium having stored thereon instructions, which may be used to program a computer system (or other electronic devices) to perform a process according to the present invention. A machine-readable medium includes any mechanism for storing or transmitting information in a form readable by a machine (e g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical or other form of propagated signals (e.g., infrared signals, digital signals, etc.)), etc.

Figure 15:
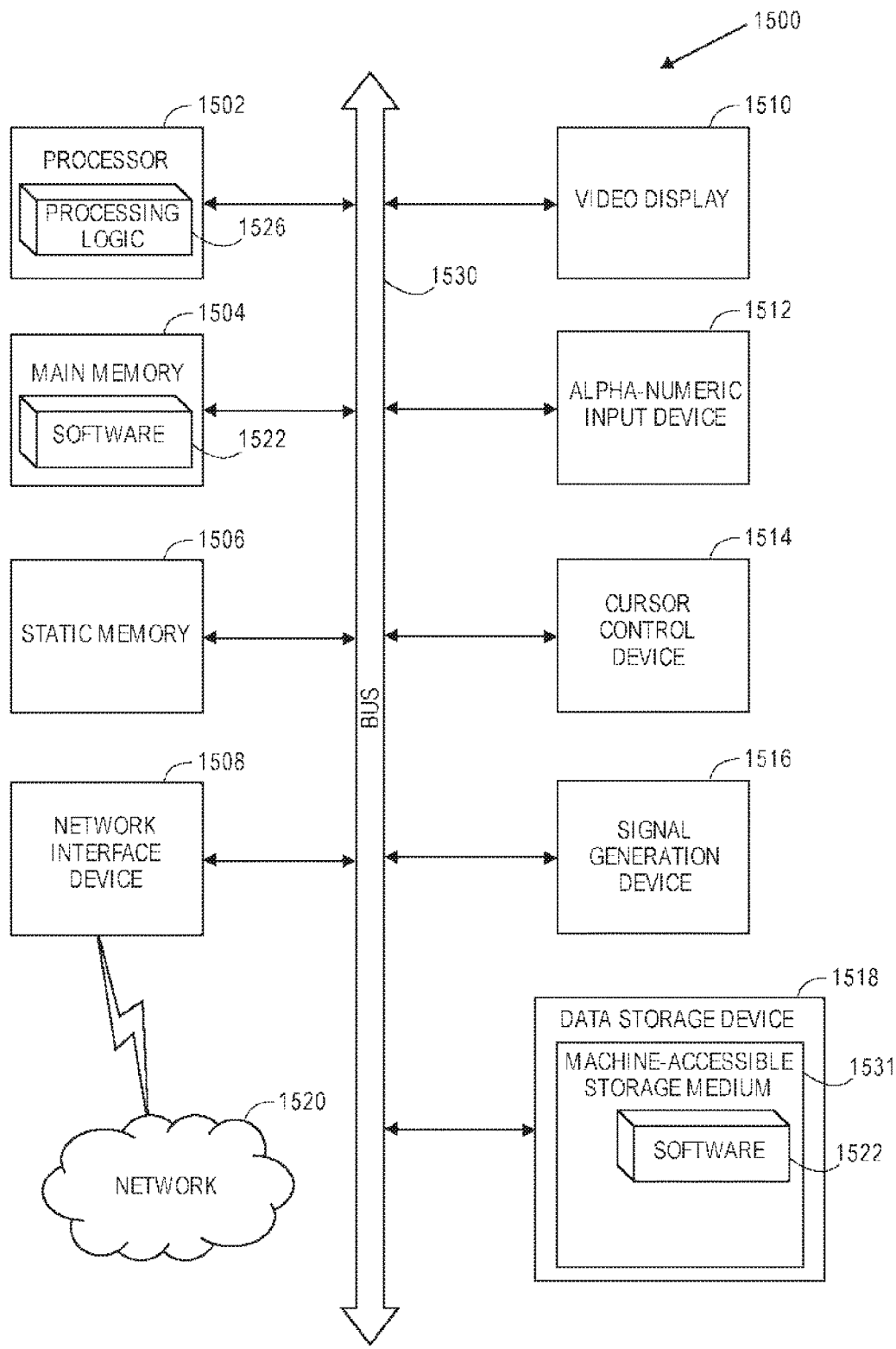
FIG. 15 illustrates a block diagram of an exemplary computer system, in accordance with an embodiment of the present invention.

FIG. 15 illustrates a diagrammatic representation of a machine in the exemplary form of a computer system 1500 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein. For example, in an embodiment, a machine is configured to execute one or more sets of instruction for measuring a sample by secondary ion mass spectrometry (SIMS). In an embodiment, the computer system 1500 is suitable for use with a system such as the SIMS system depicted and described in association with FIG. 1.

The exemplary computer system 1500 includes a processor 1502, a main memory 1504 (e.g., read-only memory (ROM), flash memory, dynamic random access memory (DRAM) such as synchronous DRAM (SDRAM) or Rambus DRAM (RDRAM), etc.), a static memory 1506 (e.g., flash memory, static random access memory (SRAM), etc.), and a secondary memory 1518 (e.g., a data storage device), which communicate with each other via a bus 1530.

Processor 1502 represents one or more general-purpose processing devices such as a microprocessor, central processing unit, or the like. More particularly, the processor 1502 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 1502 may also be one or more special-purpose processing devices such as an application specific integrated circuit (ASIC), a field programmable gate array (TPGA), a digital signal processor (DSP), network processor, or the like. Processor 1502 is configured to execute the processing logic 1526 for performing the operations discussed herein.

The computer system 1500 may further include a network interface device 1508. The computer system 1500 also may include a video display unit 1510 (e.g., a liquid crystal display (LCD) or a cathode ray tube (CRT)), an alphanumeric input device 1512 (e.g., a keyboard), a cursor control device 1514 (e.g., a mouse), and a signal generation device 1516 (e.g., a speaker).

The secondary memory 1518 may include a machine-accessible storage medium (or more specifically a computer-readable storage medium) 1531 on which is stored one or more sets of instructions (e.g., software 1522) embodying any one or more of the methodologies or functions described herein. The software 1522 may also reside, completely or at least partially, within the main memory 1504 and/or within the processor 1502 during execution thereof by the computer system 1500, the main memory 1504 and the processor 1502 also constituting machine-readable storage media. The software 1522 may further be transmitted or received over a network 1520 via the network interface device 1508.

While the machine-accessible storage medium 1531 is shown in an exemplary embodiment to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present invention. The term "machine-readable storage medium" shall accordingly be taken to include, but not be limited to, solid-state memories, and optical and magnetic media.

Thus, systems and approaches for semiconductor metrology and surface analysis using Secondary Ion Mass Spectrometry (SIMS) have been described.

In an embodiment, a secondary ion mass spectrometry (SIMS) system includes a sample stage. A primary ion beam is directed to the sample stage. An extraction lens is directed at the sample stage. The extraction lens is configured to provide a low extraction field for secondary ions emitted from a sample on the sample stage. A magnetic sector spectrograph is coupled to the extraction lens along an optical path of the SIMS system. The magnetic sector spectrograph includes an electrostatic analyzer (ESA) coupled to a magnetic sector analyzer (MSA).

In one embodiment, the sample stage includes a Faraday cup.

In one embodiment, the SIMS system further includes a plurality of detectors spaced along a plane of the magnetic sector spectrograph.

In one embodiment, the plurality of detectors is for detecting a corresponding plurality of different species from a beam of the secondary ions emitted from the sample.

In one embodiment, the SIMS system further includes a first additional ESA coupled along the optical path of the SIMS system, between the extraction lens and the ESA of the magnetic sector spectrograph, and a second additional ESA coupled along the optical path of the SIMS system, between the first additional ESA and the ESA of the magnetic sector spectrograph.

In one embodiment, the first additional ESA is configured to spread a beam of the secondary ions emitted from the sample, and wherein the second additional ESA is configured to concentrate the beam of the secondary ions received from the first additional ESA.

In one embodiment, the SIMS system further includes one or more slits along the optical path of the SIMS system, between the first additional ESA and the second additional ESA.

In one embodiment, the first additional ESA, the second additional ESA, and the one or more slits are included in a charge compensation system of the SIMS system.

In one embodiment, the first additional ESA and the second additional ESA together direct the optical path of the SIMS system from above the sample stage to below the sample.

In one embodiment, a magnet of the MSA is located below the sample stage.

In one embodiment, the low extraction field has an absolute value of at most approximately 10 Volts/mm.

In one embodiment, the SIMS system further includes a transfer robot coupled to the sample stage.

In one embodiment, the SIMS system further includes a receptacle coupled to the transfer robot, the receptacle comprises calibration standards.

In an embodiment, a method of measurement and control of the surface potential of a sample involves measuring kinetic energy of charged particles emitted from a surface of a sample. The method also involves determining a shift in kinetic energy of the charged particles. The surface potential of the surface of the sample is changed in response the shift in kinetic energy of the charged particles.

In one embodiment, the surface potential of the surface of the sample comprises adjusting a bias voltage of an electrode supporting the sample.

In one embodiment, changing the surface potential of the surface of the sample comprises directing a beam of electrons at the surface of the sample.

In one embodiment, directing the beam of electrons at the surface of the sample comprises varying a current delivered to the surface of the sample.

In one embodiment, directing the beam of electrons at the surface of the sample comprises varying an impact energy of the beam of electrons at the surface of the sample.

In one embodiment, changing the surface potential of the surface of the sample comprises directing photons of variable intensity to the sample surface.

In one embodiment, directing photons of variable intensity to the sample surface comprises generating charge carriers in the sample to vary a conductivity of the sample.

In one embodiment, directing photons of variable intensity to the sample surface comprises emitting photoelectrons from the sample to drive a sample potential to more positive.

In one embodiment, changing the surface potential of the surface of the sample comprises directing photons of variable intensity away from the sample surface.

In one embodiment, the method further includes, subsequent to changing the surface potential of the surface of the sample, performing a secondary ion mass spectrometry (SIMS) measurement of the surface of the sample.

In an embodiment, a method of determining wafer backside contact resistance involves measuring a gap distance value of a surface of a wafer based on a comparison of a main capacitive sensor electrode driven with a first drive signal and a compensating capacitive sensor electrode driven with a second drive signal that is amplitude or phase shifted as compared to the first drive signal. A value of the second drive signal is measured. The value of the second drive signal is calibrated to a reference impendence standard to determine an impedance value of the wafer to ground. A contact resistance value is determined for the surface of the wafer based on the gap distance value and the impedance value of the wafer to ground.

In one embodiment, measuring the value of the second drive signal comprises driving the compensating capacitive sensor with the second drive signal that is a 180 degree shifted version of the first drive signal, and adjusting an amplitude of the second drive signal to obtain an amplitude value when a net current of the main capacitive sensor electrode and the compensating capacitive sensor electrode is zero, and wherein calibrating the value of the second drive signal to the reference impendence standard comprises calibrating the amplitude value to the reference impendence standard.

In one embodiment, measuring the value of the second drive signal comprises driving the compensating capacitive sensor with the second drive signal that is a phase shifted version of the first drive signal, and adjusting a phase angle of the second drive signal to obtain a phase angle value when a minimum gap distance value is obtained, and wherein calibrating the value of the second drive signal to the reference impendence standard comprises calibrating the phase angle value to the reference impendence standard.

In one embodiment, measuring the value of the second drive signal comprises varying a distance of the compensating capacitive sensor electrode from the surface of the wafer to obtain minimum gap distance value, and wherein calibrating the value of the second drive signal to the reference impendence standard comprises calibrating the minimum gap distance value to the reference impendence standard.

In one embodiment, measuring the gap distance value comprises measuring the gap distance value when a net current of the main capacitive sensor electrode and the compensating capacitive sensor electrode is zero.

In one embodiment, the method further includes contacting a conductive electrode to the surface of the wafer, and directing a charged particle beam to a second surface of the wafer when the contact resistance value for the surface of the wafer is below a threshold value.

In one embodiment, directing the charged particle beam to the second surface of the wafer comprises initiating a secondary ion mass spectrometry (SIMS) measurement of the second surface of the wafer.

What is claimed is:

1. A method of measurement and control of the surface potential of a sample, the method comprising:
   measuring the distribution of kinetic energy of charged particles emitted from a surface of a sample;
   determining a shift in kinetic energy of the charged particles; and
   changing the surface potential of the surface of the sample in response the shift in kinetic energy of the charged particles.

2. The method of claim 1, wherein changing the surface potential of the surface of the sample comprises adjusting a bias voltage of an electrode supporting the sample.

3. The method of claim 1, wherein changing the surface potential of the surface of the sample comprises directing a beam of electrons at the surface of the sample.

4. The method of claim 3, wherein directing the beam of electrons at the surface of the sample comprises varying a current delivered to the surface of the sample.

5. The method of claim 3, wherein directing the beam of electrons at the surface of the sample comprises varying an impact energy of the beam of electrons at the surface of the sample.

6. The method of claim 1, wherein changing the surface potential of the surface of the sample comprises directing photons of variable intensity to the sample surface.

7. The method of claim 6, wherein directing photons of variable intensity to the sample surface comprises generating charge carriers in the sample to vary a conductivity of the sample.

8. The method of claim 6, wherein directing photons of variable intensity to the sample surface comprises emitting photoelectrons from the sample to drive a sample potential to more positive.

9. The method of claim 1, wherein changing the surface potential of the surface of the sample comprises directing photons of variable intensity away from the sample surface.

10. The method of claim 9, wherein directing photons of variable intensity away from the sample surface comprises directing the photons onto a material of high secondary electron coefficient thereby causing the sample surface to be flooded with low-energy electrons.

11. The method of claim 1, further comprising:
    subsequent to changing the surface potential of the surface of the sample, performing a secondary ion mass spectrometry (SIMS) measurement of the surface of the sample.

12. The method of claim 1, wherein the sample is a semiconductor wafer.

13. The method of claim 1, wherein measuring the distribution of kinetic energy of charged particles emitted from a surface of a sample comprises irradiating the sample with a primary ion beam and using extraction lens to collect secondary charged particles from the sample.

14. The method of claim 13, wherein using extraction lens to collect secondary charged particles comprises maintaining an extraction field of 10V/mm or less between the sample and the extraction lens.

15. The method of claim 13, wherein changing the surface potential of the surface of the sample comprises directing electron flood at the surface of the sample.

16. The method of claim 1, wherein measuring the distribution of kinetic energy comprises passing a beam of charged particles emitted from a surface of a sample through a first electrostatic analyzer and a second electrostatic analyzer, and measuring the distribution of kinetic energy of charged particles within the beam at a point between the first electrostatic analyzer and a second electrostatic analyzer.

17. The method of claim 16, further comprising providing a slit and current detectors at the point between the first electrostatic analyzer and a second electrostatic analyzer, and wherein measuring the distribution of kinetic energy of charged particles comprises measuring current at the current detectors.

18. The method of claim 1, wherein measuring the distribution of kinetic energy comprises:
- passing a beam of charged particles emitted from a surface of a sample through a first electrostatic analyzer while varying electric field in the first electrostatic analyzer to thereby cause dispersed ion beam to travel across an ion detector; and,
- intercepting by the ion detector only low and high tails of energy distribution of the ions in the dispersed ion beam.

19. The method of claim 18, further comprising passing the beam of charged particles through a second electrostatic analyzer while applying to the second electrostatic analyzer equal and opposite electric field as applied to the first electrostatic analyzer.

20. The method of claim 18, further comprising passing the beam of charged particles through a second electrostatic analyzer while applying to the second electrostatic analyzer a constant electric field.

21. The method of claim 18, further comprising placing a secondary ion blanker ahead of the first electrostatic analyzer and measuring total ion current.

22. The method of claim 1, further comprising comparing the distribution of kinetic energy to a distribution from a reference sample with known surface potential.

* * * * *